US008486696B2

(12) United States Patent
Ho et al.

(10) Patent No.: US 8,486,696 B2
(45) Date of Patent: Jul. 16, 2013

(54) CELL POPULATIONS WHICH CO-EXPRESS CD49C AND CD90

(75) Inventors: Tony W. Ho, Berwyn, PA (US); Gene C. Kopen, Wynnewood, PA (US); William F. Righter, Ridley Park, PA (US); J. Lynn Rutkowski, Wynnewood, PA (US); Joseph Wagner, West Chester, PA (US)

(73) Assignee: Garnet BioTherapeutics, Inc., Malvern, PA (US)

( * ) Notice: Subject to any disclaimer, the term of this patent is extended or adjusted under 35 U.S.C. 154(b) by 2379 days.

(21) Appl. No.: 11/054,824

(22) Filed: Feb. 10, 2005

(65) Prior Publication Data

US 2005/0233452 A1 Oct. 20, 2005

Related U.S. Application Data

(62) Division of application No. 09/960,244, filed on Sep. 21, 2001.

(51) Int. Cl.
*C12N 5/00* (2006.01)

(52) U.S. Cl.
USPC ............................ 435/374; 435/325; 435/366

(58) Field of Classification Search
None
See application file for complete search history.

(56) References Cited

U.S. PATENT DOCUMENTS

| | | | |
|---|---|---|---|
| 4,608,199 | A | 8/1986 | Caplan et al. |
| 4,609,551 | A | 9/1986 | Caplan et al. |
| 4,620,327 | A | 11/1986 | Caplan et al. |
| 4,728,641 | A | 3/1988 | Tubaro et al. |
| 5,061,620 | A | 10/1991 | Tsukamoto et al. |
| 5,197,985 | A | 3/1993 | Caplan et al. |
| 5,226,914 | A | 7/1993 | Caplan et al. |
| 5,486,359 | A | 1/1996 | Caplan et al. |
| 5,591,625 | A | 1/1997 | Gerson et al. |
| 5,643,736 | A | 7/1997 | Bruder et al. |
| 5,716,616 | A | 2/1998 | Prockop et al. |
| 5,728,581 | A | 3/1998 | Schwartz et al. |
| 5,733,542 | A | 3/1998 | Haynesworth et al. |
| 5,736,396 | A | 4/1998 | Bruder et al. |
| 5,811,094 | A | 9/1998 | Caplan et al. |
| 5,837,539 | A | 11/1998 | Caplan et al. |
| 5,855,619 | A | 1/1999 | Caplan et al. |
| 5,942,225 | A | 8/1999 | Bruder et al. |
| 5,962,323 | A | 10/1999 | Greenburger et al. |
| 6,010,696 | A | 1/2000 | Caplan et al. |
| 6,087,113 | A | 7/2000 | Caplan et al. |
| 6,174,333 | B1 | 1/2001 | Kadiyala et al. |
| 6,184,035 | B1 | 2/2001 | Csete et al. |
| 6,653,134 | B2 | 11/2003 | Prockop et al. |
| 6,719,972 | B1 | 4/2004 | Gribben et al. |
| 6,974,571 | B2 | 12/2005 | Prockop et al. |
| 7,015,037 | B1 | 3/2006 | Furcht et al. |
| 7,056,738 | B2 | 6/2006 | Prockop et al. |
| 7,521,465 | B2 | 4/2009 | Nag et al. |
| 2001/0034061 | A1 | 10/2001 | Csete et al. |
| 2001/0036642 | A1 | 11/2001 | Asselineau et al. |
| 2002/0058025 | A1 | 5/2002 | Prockop et al. |
| 2002/0146821 | A1 | 10/2002 | Sanchez-Ramos et al. |
| 2002/0168765 | A1 | 11/2002 | Prockop et al. |
| 2003/0003090 | A1 | 1/2003 | Prockop et al. |
| 2003/0003572 | A1 | 1/2003 | Anderson et al. |
| 2003/0003574 | A1 | 1/2003 | Toma et al. |
| 2003/0017587 | A1 | 1/2003 | Rader et al. |
| 2003/0039639 | A1 | 2/2003 | Prockop et al. |
| 2003/0059412 | A1 | 3/2003 | Prockop et al. |
| 2003/0059414 | A1 | 3/2003 | Ho et al. |
| 2003/0059941 | A1 | 3/2003 | Prockop et al. |
| 2003/0202966 | A1 | 10/2003 | Prockop et al. |
| 2003/0203484 | A1 | 10/2003 | Black et al. |
| 2004/0033214 | A1 | 2/2004 | Young et al. |
| 2004/0058412 | A1 | 3/2004 | Ho et al. |
| 2004/0091464 | A1 | 5/2004 | Prockop et al. |
| 2004/0107453 | A1 | 6/2004 | Furcht et al. |
| 2004/0166097 | A1 | 8/2004 | Prockop et al. |
| 2004/0208861 | A1 | 10/2004 | Prockop et al. |
| 2005/0181502 | A1 | 8/2005 | Furcht et al. |
| 2005/0283844 | A1 | 12/2005 | Furcht et al. |
| 2006/0008450 | A1 | 1/2006 | Verfaillie et al. |
| 2006/0030041 | A1 | 2/2006 | Furcht et al. |

(Continued)

FOREIGN PATENT DOCUMENTS

| | | |
|---|---|---|
| WO | WO 99/43286 | 9/1999 |
| WO | WO 00/24261 | 5/2000 |

(Continued)

OTHER PUBLICATIONS

Clayton et al., "Cells Isolated from the Human Cortical Interstitium Resemble Myofibroblasts and Bind Neutrophils in an ICAM-1-Dependent Manner," *J. Am. Soc. Nephrol.*, 8(4):604-615 (1997).

Koller et al., "Beneficial Effects of Reduced Oxygen Tension and Perfusion in Long-Term Hematopoietic Cultures," *Annals New York Academy of Sciences*, 665:105-116 (1992).

Rithidech et al., "Telomerase Activity in Mouse Myeloid Leukemic Cells and in Cells from Normal Hematopoietic Systems," *Blood Cells, Molecules, Diseases*, 27(2):496-504 (2001).

Silva et al., "The Profile of Gene Expression of Human Marrow Mesenchymal Stem Cells," *Stem Cells*, 21:661-669 (2003).

(Continued)

*Primary Examiner* — Michael G. Wityshyn
(74) *Attorney, Agent, or Firm* — Sterne, Kessler, Goldstein & Fox P.L.L.C.

(57) ABSTRACT

Substantially homogenous cells populations which co-express CD49c, CD90 and telomerase are made. In one embodiment, humans suffering from a degenerative, traumatic, acute injury, cardiac or neurological condition are treated with the substantially homogenous cells populations which co-express CD49c, CD90 and telomerase. In another embodiment, committed progenitor cells are made are made by selecting from a cultured source of a cell population which co-express CD49c and CD90 and modifying the cell population. The committed progenitor cells can be employed to treat a human suffering from a degenerative, traumatic, acute injury, cardiac or neurological condition and formulate pharmaceutical compositions.

68 Claims, 5 Drawing Sheets

U.S. PATENT DOCUMENTS

| | | |
|---|---|---|
| 2006/0288431 A1 | 12/2006 | Nakatsuji et al. |
| 2007/0224177 A1 | 9/2007 | Ho et al. |
| 2007/0231309 A1 | 10/2007 | Ho et al. |
| 2007/0264232 A1 | 11/2007 | Ho et al. |
| 2008/0119946 A1 | 5/2008 | Nugent et al. |
| 2009/0053183 A1 | 2/2009 | Kopen et al. |

FOREIGN PATENT DOCUMENTS

| | | |
|---|---|---|
| WO | WO 00/69448 | 11/2000 |
| WO | WO 01/04268 A1 | 1/2001 |
| WO | WO 01/11011 A2 | 2/2001 |
| WO | WO 01/34167 A1 | 5/2001 |
| WO | WO 01/59072 A1 | 8/2001 |
| WO | WO 01/78753 | 10/2001 |
| WO | WO 02/18401 A2 | 3/2002 |
| WO | WO 02/34889 | 5/2002 |
| WO | WO 03/025149 A2 | 3/2003 |
| WO | WO 2008/156728 A1 | 12/2008 |

OTHER PUBLICATIONS

Santalucia et al., "Hypertrophic agonists induce the binding of c-Fos to an AP-1 site in cardiac myocytes: implications for the expression of GLUT1," *Cardiovascular Research*, 59:639-648 (2003).

Akiyomo, Y. et al., "Functional Repair of Demyelinated Spinal Cord Axons in the Adult Rat by Transplantation of Clonal Neural Stem Cells Derived From Adult Human Brain," Society for Neuroscience Abstracts 25: Abstract 86.9 (1999).

Azizi, S. A., et al., "Engraftment and migration of human bone marrow stromal cells implanted in the brains of albino rats-similarities to astrocyte grafts," Proc. Natl. Acad. Sci. USA 95: 3908-3913 (1998).

Azizi, S. A., "Exploiting Non-neural Cells to Rebuild the Nervous System: From Bone Marrow to Brain," The Neuroscientist 6(5): 353-361 (2000).

Bianco, P., et al., "Bone Marrow Stromal Stem Cells: Nature, Biology, and Potential Applications," Stem Cells 19: 180-192 (2001).

Chopp, M., et al., "Spinal cord injury in rat: treatment with bone marrow stromal cell transplantation," NeuroReport 11(13): 3001-3005 (2000).

Colter, D. C. et al., "Rapid expansion of recycling stem cells in cultures of plastic-adherent cells from human bone marrow," Proc. Natl. Acad. Sci. USA 97(7): 3213-3218 (2000).

Coyle, A.J., et al., "Human Mesenchymal Stomal Cells Can Differentiate into Oligodendrocyte Lineage in Transplantation Experiments with MD Rats,"Soc. for Neurosci. Abs. 26: Abstract 415.11 (2000).

Eglitis, M. A., et al., "Hematopoietic cells differentiate into both microglia and macroglia in the brains of adult mice," Proc. Natl. Acad. Sci. USA 94: 4080-4085 (1997).

Ferrari, G., et al., "Muscle Regeneration by Bone Marrow-Derived Myogenic Progenitors," Science 279: 1528-1530 (1998).

Himes, B. T. et al., "Grafting human bone marrow stromal cells into injured spinal cord of adult rats," Society for Neuroscience Abstracts 25: Abstract 86.11 (1999).

Kopen, G. C., et al., "Marrow stromal cells migrate throughout forebrain and cerebellum, and they differentiate into astrocytes after injection into neonatal mouse brains," Proc. Natl. Acad. Sci. USA 96: 10711-10716 (1999).

Li, J., et al., "Nontransformed colony-derived stromal cell lines from normal human marrows. II. Phenotypic characterization and differentiation pathway," Experimental Hematology 23: 133-141 (1995).

Liechty, K. W., et al., "Human mesenchymal stem cells engraft and demonstrate site-specific differentiation after in utero transplantation in sheep," Nature Medicine 6(11): 1282-1286 (2000).

Majumdar, M .K., et al., "Phenotypic and Functional Comparison of Cultures of Marrow-Derived Mesenchymal Stem Cells (MSCs) and Stromal Cells," J. Cell. Phys. 176: 57-66 (1998).

Pereira, M. K., et al., "Cultured adherent cells from marrow can serve as long-lasting precursor cells for bone, cartilage, and lung in irradiated mice," Proc. Natl. Acad. Sci. USA 92: 4857-4861 (1995).

Phinney, D. G., et al., "Donor Variation in the Growth Properties and Osteogenic Potential of Human Marrow Stromal Cells," J. Cell. Biochem. 75: 424-436 (1999).

Phinney, D. G., et al., "Plastic Adherent Sromal Cells From the Bone Marrow of Commonly Used Strains of Inbred Mice: Variations in Yield, Growth, and Differentiation," J. Cell. Biochem. 72: 570-585 (1999).

Pittenger, M. F., et al., "Multilineage Potential of Adult Human Mesenchymal Stem Cells," Science 284: 143-147 (1999).

Prockop, D. J., "Marrow Stromal Cells as Stem Cells for Nonhematopoietic Tissues," Science 276: 71-74 (1997).

Roisen, F. J., et al., "Murine and Human Adult Olfactory Neuroepithelial Stem Cells," Society for Neuroscience Abstracts 26: Abstract 312.7 (2000).

Sanchez-Ramos, J., et al., "Adult Bone Marrow Stromal Cells Differentiate into Neural Cells in Vitro," Experimental Neurology 164: 247-256 (2000).

Sanchez-Ramos, J., et al., "Bone marrow stromal cells grafgted into adult rat brain migrate, organize in architectonic patterns and express neuronal markers," Neurology 52(6 Suppl. 2): A14, S06.001 (1999).

Schwartz, E. J., et al., "Multipotential Marrow Stromal Cells Transduced to Produce 1-DOPA: Engraftment in a Rat Model of Parkinson Disease," Human Gene Therapy 10: 2539-2549 (1999).

Taupin, P., et al., "FGF-2-Responsive Neural Stem Cell Proliferation Requires CCg, a Novel Autocrine/Paracrine Cofactor," Neuron 28: 385-397 (2000).

Woodbury, D., et al., "Adult Rat and Human Bone Marrow Stromal Cells Differentiate Into Neurons," J. Neurosci. Res. 61: 364-370 (2000).

Woodbury, D., et al., "Adult Rat and Human Bone Marrow Stromal Cells Differentiate Into Neurons," Society for Neuroscience Abstracts 26: Abstract 312.9 (2000).

Ashhurst, D.E., et al., "The collagens and glycosaminoglycans of the extracellular matrices secreted by bone marrow stromal cells cultured in vivo in diffusion chambers," J. Orthop Res 8(5):741-749 (1990).

Ashton, B.A., et al., "Formation of Bone and Cartilage by Marrow Stromal Cells in Diffusion Chambers in Vivo," Clinical Orthopaedics and Related Research, 151:294-307 (1990).

Ashton, B.A., et al., "Distribution of Fibroblastic Colony-Forming Cells in Rabbit Bone Marrow and Assay of their Osteogenic Potential by an in vivo Diffusion Chamber Method," Calcif Tissue Int. 36:83-86 (1984).

Bab, I., et al., "Assessment of an in vivo Diffusion Chamber Method as a Quantitative Assay for Osteogenesis," Calcif Tissue Int 36:77-82 (1984).

Bab, I., et al., "Osteogenesis in in vivo diffusion chamber cultures of human marrow cells," Bone and Mineral, 4:373-386 (1988).

Bab, I., et al., "Ultrastructure of Bone and Cartilage Formed in vivo in Diffusion Chambers," Clinical Orthopaedics and Related Research, Section III:243-254 (1984).

Benayahu, D., et al., "Bone Marrow-Derived Stromal Cell Line Expressing Osteoblastic Phenotype in Vitro and Osteogenic Capacity in Vivo," Journal of Cellular Physiology 140:1-7 (1989).

Budenz, R.W. et al., "Osteogenesis and Leukopoieses within Diffusion-Chamber Implants of Isolated Bone Marrow Subpopulations," The American journal of Anatomy 159:455-474 (1980).

Diduch, D.R., et al, "Two cell lines from bone marrow that differ in terms of collagen synthesis, osteogenic characteristics, and matrix mineralization," Journal of Bone & Joint Surgery 75:92-105 (1993).

Friedenstein, A.J., et al., "Bone marrow osteogenic stem cells: in vitro cultivation and transplantation in diffusion chambers," Cell Tissue Kinet. 20:263-272 (1987).

Gundle, R., et al., "Human Bone Tissue Formation in Diffusion Chamber Culture in vivo by Bone-Derived Cells and Marrow Stromal Fibroblastic Cells," Bone 16(6):597-601 (1995).

Haynesworth, S.E., et al., "Cell Surface Antigens on Human Marrow-Derived Mesenchymal Cells are Detected by Monoclonal Antibodies," Bone 13:69-80 (1992).

Haynesworth, S.E., et al., "Characterization of Cells with Osteogenic Potential from Human Marrow," Bone 13:81-88 (1992).

Kataoka, H., et al., "Transplant of bone marrow and muscle-derived connective tissue cultures in diffusion chambers for bioassay of bone morphogenetic protein," Clinical Orthopaedics and Related Research 286:262-70 (1993).

Krebsbach, P.H., et al., "Bone Formation in vivo: Comparison of Osteogenesis by Transplanted Mouse and Human Marrow Stromal Fibroblasts," Transplantation 63(8):1059-1069 (1997).

Lennon, D.P., et al., "Cultivation of Rat Marrow-Derived Mesenchymal Stem Cells in Reduced Oxygen Tension: Effects on in Vitro and in Vivo Osteochondrogenesis," Journal of Cellular Physiology 187:345-355 (2001).

Mardon, H.J., et al., "Development of osteogenic tissue in diffusion chambers from early precursor cells in bone marrow of adult rats," Cell Tissue Research, 250:157-165 (1987).

Quinones, R.R., "Hematopoietic Engraftment and Graft Failure After Bone Marrow Transplantation," The American Journal of Pediatric Hematology/Oncology 15(1):3-17 (1993).

Thomson, B.M., et al., "Preliminary characterization of porcine bone marrow stromal cells: skeletogenic potential, colony-forming activity, and response to dexamethasone, transforming growth factor beta, and basic fibroblast growth factor," J. Bone Min Res 8(10): 1173-1183 (1993).

Ross, J.A., et al., "Phenotypic Mapping of Human Mesothelial Cells," Medline Abstract, Accession No. 200113945, Document No. 20113945, Adv. Peritoneal Dialysis, 14:25-30 (1998).

Cooper, et al., J. Dent. Res. 2001. 80(1):314-320.

Christian van den Bos, et al., Cell Tissue Res. 1998. 293:463-470.

Gartel, et al., Exp. Cell Res. 1999. 246(2):280-289.

Batinic, D., et al., "Relationship Between Differing Volumes of Bone Marrow Aspirates and Their Cellular Composition," Bone Marrow Transplantation, 6:103-107 (1990).

Bruder, S.P., et al., "Growth Kinetics, Self-Renewal, and the Osteogenic Potential of Purified Human Mesenchymal Stem Cells During Extensive Subcultivation and Following Cryopreservation," Journal of Cellular Biochemistry, 64:278-294 (1997).

Caplan, A.I. and Bruder, Scott P., "Cell and Molecular Engineering of Bone Regeneration." In Principles of Tissue Engineering, R.P. Lanza et al., eds. (Texas: R.G. Lanes Company), Chapter 37: 603-618, (1997).

Lodie, T.A., et al., "Systematic Analysis of Reportedly Distinct Populations of Multipotent Bone Marrow-Derived Stem Cells Reveals a Lack of Distinction," Tissue Engineering, 8(5):739-751 (2002).

Müller-Ehmsen, Jochen, et al., "Rebuilding a Damaged Heart: Long-Term Survival of Transplanted Neonatal Rat Cardiomyocytes After Myocardial Infarction and Effect on Cardiac Function," Circulation, pp. 1720-1726 (2002).

Muschler, G.F., et al., "Aspiration to Obtain Osteoblast Progenitor Cells From Human Bone Marrow: The Influence of Aspiration Volume," JBJA Journal of Bone and Joint Surgery-American, 79A:1699-1709 (1997).

Pittenger, M.F., et al., Multilineage Potential of Adult Human Mesenchymal Stem Cells, Supplementary Material, http://www.Sciencemag.org/feature/data/983855.dt I (Apr. 2, 1999).

Van den Bos, C., et al., "Human Mesenchymal Stem Cells Respond to Fibroblast Growth Factors," Human Cell, 10(1):45-50 (1997).

Abu-Abeeleh, M., et al., "Efficacy of Human Adipose Tissue-derived Stem Cells in Cardiac Muscle Repair in an Experimental Acute Myocardial Infarction Model Using Nude Rats (Crl:NIH-Fox1$^{RNU}$)," Comp. Clin. Pathol. 19:593-600, Springer-Verlag London Limited, England (Nov. 2009).

Alberts, B., et al., eds., Molecular Biology of the Cell, Second Edition, p. 746, Garland Publishing Inc., United States (1989).

Aldhous, P. and Reich, E.S., "Flawed Stem Cell Data Withdrawn," NewScientist.com, accessed at http://www.newscientist.com/article.ns?id=mg19325915.200, accessed on Feb. 15, 2007, 2 pages.

Aldhous, P. and Reich, E.S., "Fresh Questions on Stem Cell Findings," NewScientist.com, accessed at http://www.newscientist.com/article.ns?id=mg19325964.600, accessed on Mar. 21, 2007, 3 pages.

Al-Khaldi, A., et al., "Postnatal Bone Marrow Stromal Cells Elicit a Potent VEGF-Dependent Neoangiogenic Response In Vivo," Gene Ther. 10:621-629, Nature Publishing Group, England (Apr. 2003).

Annex, B.H., "Therapeutic Angiogenesis: A Treatment for the New Millennium or Passing Fad?" Cardiol. Rounds 6:1-6, Snell Medical Communication Inc., United States (Jan. 2002).

Aprikyan, A.A., et al., "Erratum," Exp. Hematol. 34:1771-1772, Elsevier Inc., Netherlands (Dec. 2006).

Baksh, D., et al., "Adult Mesenchymal Stem Cells: Characterization, Differentiation, and Application in Cell and Gene Therapy," J. Cell. Mol. Med. 8:301-316, Wiley-Blackwell, England (Jul. 2004).

Bao, P., et al., "The Role of Vascular Endothelial Growth Factor in Wound Healing," J. Surg. Res. 153:347-358, Academic Press, United States (May 2009).

Boodhwani, M. and Sellke, F.W., "Therapeutic Angiogenesis in Diabetes and Hypercholesterolemia: Influence of Oxidative Stress," Antioxid. Redox Signal. 11:1945-1959, Mary Ann Liebert, Inc., United States (Aug. 2009).

Brissova, M. and Powers, A.C., "Revascularization of Transplanted Islets—Can It Be Improved?" Diabetes 57:2269-2271, American Diabetes Association, United States (Sep. 2008).

Carmeliet, P., "Angiogenesis in Health and Disease," Nat. Med 9:653-660, Nature Publishing Group, England (Jun. 2003).

Celis, J.E., ed. Cell Biology: A Laboratory Handbook, Second Edition, vol. 1, pp. 6-11, Academic Press, United States (1998).

Chamberlain, G., et al. "Concise Review: Mesenchymal Stem Cells: Their Phenotype, Differentiation Capacity, Immunological Features, and Potential for Homing," Stem Cells 25:2739-2749, AlphaMed Press, United States (Jul. 2007).

Check, E., "Stem Cells: The Hard Copy," Nature 446:485-486, Nature Publishing Group, England (Mar. 2007).

Check, E., "Stem-Cell Paper Corrected," Nature 447:763, Nature Publishing Group, England (Jun. 2007).

Chi, K.R., "Adult Stem Cell Figure Retracted," The-Scientist.com, accessed at http://www.the-scientist.com/news/home/53279/, accessed on Jun. 26, 2007, 8 pages (Jun. 2007).

Dai, W. and Kloner, R.A., "Experimental Cell Transplantation Therapy in Rat Myocardial Infarction Model Including Nude Rat Preparation," Methods Mol. Biol. 660:99-109, Humana Press, New York City, United States, (Aug. 2010).

Eskin, S.G., et al., "Human Smooth Muscle Cells Culture From Artherosclerotic Plaques and Uninvolved Vessel Wall," In Vitro 17:713-8, Tissue Culture Assn., United States (1981), abstract from NCBI PubMed, PMID No. 7327599.

Favia, G., et al., "Accelerated Wound Healing of Oral Soft Tissues and Angiogenic Effect Induced by a Pool of Amino Acids Combined to Sodium Hyaluronate (AMINOGRAM®)," J. Biol. Regul. Homeost. Agents 22:109-116, BIOLIFE, s.a.s., Italy (Apr. 2008).

Frantz, S., et al., "Innate Immunity and Angiogenesis," Circ. Res. 96:15-26, Amercian Heart Association, Inc., United States (Jan. 2005).

Freed, J., "Study on Uses for Adult Stem Cells was Flawed, Panel Says," Deseretnews.com, accessed at http://www.deseretnews.com/dn/print/1,1442,660198505,00.html, accessed on May 17, 2007, 2 pages (Feb. 2007).

Frödin, M. and Gammeltoft, S., "Insulin-like Growth Factors Act Synergistically with Basic Fibroblast Growth Factor and Nerve Growth Factor to Promote Chromaffin Cell Proliferation," Proc. Natl. Acad. Sci. U.S.A. 91:1771-1775, National Academy of Sciences, United States (1994).

Gao, J., et al., "Tissue-Engineered Fabrication of an Osteochondral Composite Using Rat Bone Marrow-Derived Mesenchymal Stem Cells," Tissue Eng. 7:363-371, Mary Ann Liebert, Inc., United States (Aug. 2001).

Goldman, S. and Raya, T.E., "Rat Infarct Model of Myocardial Infarction and Heart Failure," J. Card. Fail. 1:169-177, Churchill Livingstone, United States (1995).

Greenhalgh, D.G., et al., "Synergistic Actions of Platelet-derived Growth Factor and the Insulin-like Growth Factors In Vivo—Enhancement of Tissue Repair in Genetically Diabetic Mice," Wound Repair Regen. 1:69-81, Blackwell Science, United States (1993).

Hayflick, L. and Moorhead, P.S., "The Serial Cultivation Of Human Diploid Cell Strains," Exp. Cell Res. 25:585-621, Academic Press, United States (1961).

Himes, B.T., et al., "Recovery of Function Following Grafting of Human Bone Marrow-derived Stromal Cells into the Injured Spinal Cord," Neurorehabil. Neural Repair 20:278-296, Sage Publications, United States (Jun. 2006), abstract from NCBI PubMed, PMID No. 16679505.

Jennemann, R., et al., "Specific Immunization Using Keyhole Limpet Hemocyanin-Ganglioside Conjugates," *J. Biochem.* 115:1047-1052, Oxford University Press, England (1994).

Jiang, Y. et al., "Errata: Multipotent Progenitor Cells Can Be Isolated From Postnatal Murine Bone Marrow, Muscle, and Brain," *Exp. Hematol.* 34:809, Elsevier Science Inc., Netherlands (Jun. 2006).

Jiang, Y. et al., "Multipotent Progenitor Cells Can Be Isolated From Postnatal Murine Bone Marrow, Muscle, and Brain," *Exp. Hematol.* 30:896-904, Elsevier Science Inc., Netherlands (Aug. 2002).

Jiang, Y. et al., "Pluripotency of Mesenchymal Stem Cells Derived From Adult Marrow," *Nature* 418:41-49, Nature Publishing Group, England (Jul. 2002).

Jiang, Y. et al., "Corrigendum: Pluripotency of Mesenchymal Stem Cells Derived From Adult Marrow," *Nature* 447:879-880, Nature Publishing Group, England (Jun. 2007).

Ju, Y-J., et al., "Effects of Local Administration of Vascular Endothelial Growth Factor on Properties of the in Situ Frozen-Thawed Anterior Cruciate Ligament in Rabbits," *Am. J. Sports Med.* 34:84-91, Wiliams & Wilkins, United States (Jan. 2006).

Kaigler, D., et al., "Role of Vascular Endothelial Growth Factor in Bone Marrow Stromal Cell Modulation of Endothelial Cells," *Tissue Eng.* 9:95-103, Mary Ann Liebert, Inc., United States (Feb. 2003).

Kolf, C.M., et al., "Mesenchymal Stromal Cells: Biology of Adult Mesenchymal Stem Cells: Regulation of Niche, Self-renewal and Differentiation," *Arthritis Res. Ther.* 9:204, BioMed Central, England (Feb. 2007).

Lee, K.A., et al., "Increased Mesenchymal Cell Density Accompanies Induction of Tropoelastin Expression in Developing Elastic Tissue," *Dev. Dyn.* 200:53-67, Wiley-Liss, Inc., United States (1994).

Lee, K.D., et al., "In Vitro Hepatic Differentiation of Human Mesenchymal Stem Cells," *Hepatology* 40:1275-1284, Williams & Wilkins, United States (Dec. 2004).

Lewis, R.J., Sr., *Hawley's Condensed Chemical Dictionary*, Twelfth Edition, p. 28, Van Nostrand Reinhold, United States (1993).

Lu, B., et al., "Human Adult Bone Narrow-derived Somatic Cells Rescue Vision in a Rodent Model of Retinal Degeneration," *Exp. Eye Res.* 91:449-455, Academic Press, England (Jul. 2010).

Lynch, S.E., et al., "Growth Factors in Wound Healing—Single and Synergistic Effects on Partial Thickness Forcine Skin Wounds," *J. Clin. Invest.* 84:640-646, The American Society for Clinical Investigation, Inc., United States (1989).

Morris, W., ed., *The American Heritage Dictionary of the English Language* New College Edition, pp. 353, Houghton Mifflin Company, United States (1976).

Murry, C.E., et al., "Haematopoietic Stem Cells Do Not Transdifferentiate Into Cardiac Myocytes in Myocardial Infarcts," *Nature* 428:664-668, Nature Publishing Group, England (Apr. 2004).

Okura, H., et al., "Cardiomyoblast-like Cells Differentiated from Human Adipose Tissue-Derived Mesenchymal Stem Cells Improve Left Ventricular Dysfunction and Survival in a Rat Myocardial Infarction Model," *Tissue Eng. Part C Methods* 16:417-425, Mary Ann Liebert, Inc., United States (Jun. 2010).

Parnas, D. and Linial, M., "Culture Density Regulates Both the Cholinergic Phenotype and the Expression of the CNTF Receptor in P19 Neurons," *J. Mol. Neurosci.* 8:115-130, Humana Press, United States (1997).

Peter, S.J., et al., "Marrow Stromal Osteoblast Function on a Poly(propylene Fumarate)/Beta-tricalcium Phosphate Biodegradable Orthopaedic Composite," *Biomaterials* 21:1207-1213, Elsevier Science, England (Jun. 2000), abstract from NCBI PubMed, PMID No. 10811302.

Reinecke, H., et al., "Skeletal Muscle Stem Cells Do Not Transdifferentiate Into Cardiomyocytes After Cardiac Grafting," *J. Mol. Cell. Cardiol.* 34:241-249, Academic Press, England (Feb. 2002).

Reynolds, L.J., et al., "Density and Substrata are Important in Lung Type II Cell Transdifferentiation In Vitro," *Int. J. Biochem. Cell Biol.* 31:951-960, Elsevier, Netherlands (1999).

Seidel, C.L., et al., "Effect of Seeding Density and Time in Culture on Vascular Smooth Muscle Cell Proteins," *Am. J Physiol.* 254:C235-C242, American Physiological Society, United States (1988), abstract from NCBI PubMed, PMID No. 3279797.

Shirinsky, V.P., et al., "Density-Related Expression of Caldesmon and Vinculin in Cultured Rabbit Aortic Smooth Muscle Cells," *Exp. Cell. Res.* 194:186-189, Academic Press, United States (1991), abstract from NCBI PubMed, PMID No. 1902791.

Sigma-Aldrich, Inc., "Sigma-Aldrich Leukocyte Seperation (Procedure No. 1119)," pp. 1, Sigma-Aldrich, Inc., United States (Sep. 2003).

Sun, Z., et al., "Human Angiogenic Cell Precursors Restore Function in the Infarcted Rat Heart: A Comparison of Cell Delivery Routes," *Eur. J. Heart Fail.* 10:525-533, Elsevier Science, Netherlands (Jun. 2008).

Unemori, E.N., et al., "Interleukin-1 and Transforming Growth Factor-$\alpha$: Synergistic Stimulation of Metalloproteinases, PGE2, and Proliferation in Human Fibroblasts," *Exp. Cell Res.* 210:166-171, Academic Press, United States (1994).

Verfaillie, C. and Jiang, Y., "Errata," *Exp. Hematol.* 34:809, Elsevier Inc., Netherlands (Jun. 2006).

Voelkel, N.F., et al., "Angiogenesis in Chronic Lung Disease," *Chest* 131:874-879, American College of Chest Physicians, United States (Mar. 2007).

Voronov, E., et al., "IL-1 is Required for Tumor Invasiveness and Angiogenesis," *Proc. Natl. Acad. Sci. U.S.A.* 100:2645-2650, National Academy of Sciences, United States (Mar. 2003).

Wade, N., "Panel Finds Flawed Data in a Major Stem Cell Report," NYTimes.com, accessed at http://www.nytimes.com/2007/02/28/science/28stem.html?ei=5070&en=b124e855015b1933&ex=117954, available on Feb. 28, 2007, 2 pages.

Xiong, Y., et al., "Neurorestorative Treatments for Traumatic Brain Injury," *Discov. Med.* 10:434-442, Discovery Medicine, United States (Nov. 2010).

Xu, R., et al., "Serum Supplement, Inoculum Cell Density, and Accessory Cell Effects are Dependent on the Cytokine Combination Selected to Expand Human HPCs Ex Vivo," *Transfusion* 40:1299-1307. American Association of Blood Banks, United States (Nov. 2000), abstract from NCBI PubMed, PMID No. 11099656.

Yang, H., et al., "IL-1 Receptor Antagonist-Mediated Therapeutic Effect in Murine Myasthenia Gravis is Associated wth Suppressed Serum Proinflammatory Cytokines, C3, and Anti-Acetylcholine Receptor IgG1," *J. Immunol.* 175:2018-2025, American Association of Immunologists, United States (Aug. 2005).

Yu, C., et al., "The Different Effects of TGF-$\beta$1, VEGF and PDGF on the Remodeling of the Anterior Cruciate Ligament Graft," in *Targets in Gene Therapy*, pp. 389-396, Y. You, ed., InTech, Croatia (Aug. 2011).

Zevin, S., et al., "Nicotine Transport in a Human Choriocarcinoma Cell Line (JAR)," *J. Pharm. Sci.* 87:702-706, American Pharmaceutical Assn., United States (1998), abstract from NCBI PubMed, PMID No. 9607946.

European Search Report dated Oct. 30, 2007.

Reyes et al., "Purification and Ex Vivo Expansion of Postnatal Human Marrow Mesodermal Progenitor Cells," Blood, 2001 98:2615-2625.

CELL POPULATIONS WHICH CO-EXPRESS CD49C AND CD90

RELATED APPLICATION

This application is a divisional of U.S. application Ser. No. 09/960,244, filed Sep. 21, 2001. The entire teachings of the above application are incorporated herein by reference.

BACKGROUND OF THE INVENTION

A number of conditions and diseases of the central (brain and spinal cord) and peripheral nervous system adversely affect humans. These conditions and diseases include, for example, spinal cord injury, amyotrophic lateral sclerosis (ALS), Parkinson's disease, stroke, traumatic brain injury, brain tumors and Fabry Disease. Clinical management strategies frequently focus of the prevention of further neurological damage or injury rather than replacement or repair of the damaged neurological tissue (e.g., neurons, glial cells); include treatment with exogenous steroids and synthetic, non-cellular pharmaceutical drugs; and have varying degrees of success which may depend on the continued administration of the steroid or synthetic drug.

For example, the majority of spinal cord injuries are compression injuries with the remaining cases involving complete transection of the spinal cord. Current therapeutic treatments for spinal cord injury include the prevention of additional spinal cord injury by physically stabilizing the spine through surgical and non-surgical procedures and by inhibiting the inflammatory response with steroidal therapy. Thus, there is a need to develop new, improved and effective methods of treatment for neurological diseases and conditions in humans.

SUMMARY OF THE INVENTION

The present invention relates to a population of cells which co-express CD49c and CD90 and methods of treating neurological conditions in humans with these populations of cells.

In one embodiment, the invention is a substantially homogenous cell population which co-express CD49c, CD90 and telomerase.

In another embodiment, the invention is a substantially homogenous cell population which co-express CD49c and CD90, but does not express bone sialoprotein (BSP).

In still another embodiment, the invention includes a method of making a substantially homogenous cell population which co-express CD49c and CD90 by culturing a source of the cell population a seeding cell density of less than about 100 cells/cm$^2$ under a low oxidative stress condition and selecting from the cultured source of the cell population, cells which co-express CD49c and CD90.

In a further embodiment, the invention includes a method of making a substantially homogenous cell population which co-express CD49c and CD90 by culturing a source of the cell population at a seeding density of less than about 100 cells/cm$^2$ under a low oxidative stress condition; and selecting from the cultured source of the cell population, cells which co-express CD49c and CD90.

In another embodiment, the invention is a method of making a substantially homogenous cell population which co-express CD49c and CD90 by culturing a source of the cell population at a seeding density of less than about 50 cells/cm$^2$ under a low oxidative stress condition; and selecting from the cultured source of the cell population, cells which co-express CD49c and CD90.

In still another embodiment, the invention is a method of making a substantially homogenous cell population which co-express CD49c and CD90 by culturing a source of the cell population at a seeding density of less than about 30 cells/cm$^2$ under a low oxidative stress condition; and selecting from the cultured source of the cell population, cells which co-express CD49c and CD90.

A further embodiment of the invention is a method of making a substantially homogenous cell population which co-express CD49c and CD90 by culturing a source of the cell population at a seeding density of less than about 75,000 cells/cm$^2$ under a low oxidative stress condition to produce an adherent cell population and culturing the adherent cell population at a seeding density of less than about 100 cells/cm$^2$ under a low oxidative stress condition. Cells which co-express CD49c and CD90 are selected from the cultured adherent cell population.

Another embodiment of the invention includes a method of making a substantially homogenous cell population which co-express CD49c and CD90 by culturing a source of the cell population at a seeding cell density of less than about 50 cells/cm$^2$ under a low oxygen condition and selecting from the cultured source of the cell population, cells which co-express CD49c and CD90.

In yet another embodiment, the invention includes a method of making a substantially homogenous cell population which co-express CD49c and CD90 by culturing a source of the cell population at a seeding cell density of less than about 30 cells/cm$^2$ under a low oxygen condition and selecting from the cultured source of the cell population, cells which co-express CD49c and CD90.

In a further embodiment, the invention is a method of making a substantially homogenous cell population which co-express CD49c and CD90 by culturing a source of the cell population at a seeding cell density of less than about 75,000 cells/cm$^2$ under a low oxygen condition to produce an adherent cell population; culturing the adherent cell population at an initial density of less than about 100 cells/cm$^2$ under a low oxygen condition; and selecting from the cultured adherent cell population, cells which co-express CD49c and CD90.

Another embodiment of the invention is a method of treating a human suffering from a degenerative or acute injury condition, comprising the step of administering to the human a substantially homogenous cell population which co-express CD49c and CD90.

In yet another embodiment, the invention includes a method of treating a human suffering from a neurological condition, comprising the step of administering to the human a substantially homogenous cell population which co-express CD49c and CD90.

In still another embodiment, the invention is a method of treating a human suffering from a cardiac condition to the human a substantially homogenous cell population which co-express CD49c and CD90.

An additional embodiment of the invention is a method of treating a human suffering from a neurological condition by culturing a source of a cell population at a seeding cell density of less than about 100 cells/cm$^2$ under a low oxygen condition; selecting from the cultured source of the cell population, a population of cells which co-express CD49c and CD90; and administering the population of cells which co-express CD49c and CD90 to the human.

In yet an additional embodiment, the invention includes a method of treating a human suffering from a neurological condition, comprising culturing a source of a cell population; selecting from the cultured source of the cell population, a population of cells which co-express CD49c and CD90; and administering the population of cells which co-express CD49c and CD90 to the human.

In still another embodiment, the invention is a method of making a committed progenitor cell, comprising culturing a source of a cell population; selecting from the cultured source of the cell population, cells which co-express CD49c and CD90; and modifying the cells which co-express CD49c and CD90 to become committed progenitor cells.

An additional embodiment of the invention includes a method of treating a human suffering from a neurological condition, comprising culturing a source of a cell population; selecting from the cultured source of the cell population, cells which co-express CD49c and CD90; modifying the cells which co-express CD49c and CD90 to become a committed progenitor cell; and administering the modified cells to the human.

In another embodiment, the invention relates to a method of treating a human suffering from a degenerative or acute injury condition by administering to the human a substantially homogenous cell population which co-express CD49c, CD90 and telomerase.

In another embodiment, the invention provides a pharmaceutical composition comprising a substantially homogenous cell population which co-express CD49c and CD90.

In yet another embodiment, the invention provides a pharmaceutical composition comprising a substantially homogenous cell population which co-express CD49c, CD90 and telomerase.

A further embodiment of the invention is a method of treating a human suffering from a neurological condition, comprising the step of administering to the human a substantially homogenous cell population which co-express CD49c, CD90 and telomerase.

In another embodiment, the invention is a method of treating a human suffering from a degenerative or acute injury condition, comprising the step of administering to the human a substantially homogenous cell population which co-express CD49c and CD90, but does not express bone sialoprotein (BSP).

In yet another embodiment, the invention is a method of treating a human suffering from a neurological condition, comprising the step of administering to the human a substantially homogenous cell population which co-express CD49c and CD90, but does not express bone sialoprotein.

The invention described herein provides a substantially homogenous population of cells for treating a condition or disease in a human. Advantages of the cell based therapies of the claimed invention include, for example, incorporation of the cells into the tissue (e.g., central nervous system tissue, peripheral nervous system tissue, cardiac tissue); the incorporated cells have the potential to differentiate or develop into neuronal, glial or other cells (e.g., cardiac muscle) to replace or facilitate repair of the damaged, traumatized or degenerating tissue thereby resulting in a more permanent treatment of the degenerative, acute injury, traumatized, neurological or cardiac condition; and the ability to employ characterized reproducible populations of cells in treatment regimens. The cells of the invention have the potential to secret beneficial cytokines and trophic factors (e.g., BDNF, IL-6, NGF and MCP-1).

Thus, treatment of humans with populations of cells which co-express CD49c and CD90 can potentially reverse, diminish or repair the loss due to a degenerative, acute injury, neurological or cardiac condition in a human, thereby increasing the quality of life and life expectancy for the human.

DETAILED DESCRIPTION OF THE INVENTION

Figure 1A:
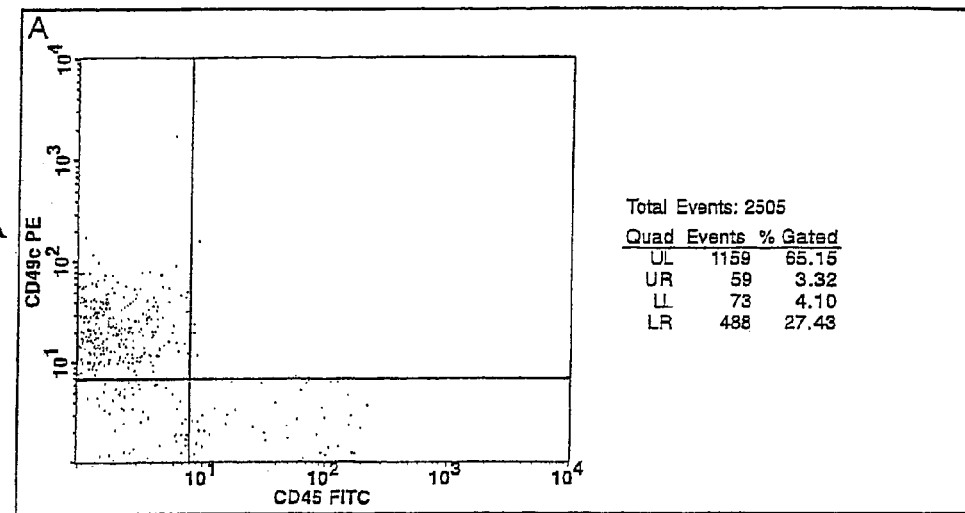
FIGS. 1A, 1B and 1C illustrate the flow cytometric analysis of cell populations in the Master and Working Cell Banks generated from a bone marrow aspirate following red blood cell lysis.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to a substantially homogeneous cell population of cells which co-express CD49c and CD90. The invention also relates to a substantially homogeneous cell population of cells which co-express CD49c, CD90 and telomerase. The invention further relates to a substantially homogeneous cell population of cells which co-express CD49c and CD90, but does not express bone sialoprotein (BSP).

"Substantially homogenous" as used herein refers to a population of cells wherein the majority (e.g., between about 100% to about 70%) of the total number of cells have a specified characteristic of interest (e.g., co-express CD49c and CD90; co-express CD49c, CD90 and telomerase; co-express of CD49c and C90 with minimal expression of CD34 and/or CD45).

In one embodiment, the substantially homogenous population of cells which co-express CD49c and CD90 is a population of cells wherein between about 80% to about 90% of the cells co-express the cell surface antigens CD49c and CD90. In another embodiment, the substantially homogenous population of cells is a population of cells wherein between about 70% to about 80% of the cells co-express the cell surface antigens CD49c and CD90.

"Co-express," as used herein, refers to the simultaneous detection of two or more molecules, e.g., CD49c and CD90, on or in a single cell. Techniques to detect co-expression of CD49c and CD90 in cells (e.g., bone marrow stromal cells) are well established. For example, co-expression of CD49c and CD90 on a cell can be detected by multiple color cytometric analysis. CD49c can be detected employing a fluorescein labeled probe and CD90 can be detected employing a Texas red probe. The CD49c and CD90 cell surface antigens can be visualized with the aid of a flow cytometer equipped with multiple filters capable of detecting the multiple colors. Techniques to detect the molecules of interest can also include ELISA, RIA, immunoflouresence microscopy and quantitative PCR.

In another embodiment, the invention is a substantially homogenous cell population of the invention which co-express CD49c and CD90, but does not express bone sialoprotein.

The substantially homogenous cell population of the invention which co-express CD49c and CD90 has a doubling time less than between about 144 hours to about 48 hours. In one embodiment, the doubling time of the cell population is less than about 144 hours. In another embodiment, the doubling time of the cell population is less than about 72 hours. In still another embodiment, the doubling time is less than about 48 hours. The doubling time of the cells of the invention can be varied depending on, for example, the density of the cells in culture (e.g., 100 cells/cm$^2$) and/or the concentration of oxygen employed to culture the cells (e.g., a low oxygen concentration such as about 5% oxygen).

The substantially homogenous cell population which co-express CD49c and CD90 can have the potential to differentiate into a preselected phenotype (e.g., chondrocytes, astrocytes, oligodendrocytes, neurons, bone, osteoclasts, osteoblasts, cardiomyocytes, pancreatic islet cells, skeletal muscle, smooth muscle, hepatocytes and retinal ganglial cells). The potential to differentiate into a preselected phenotype refers to the ability of the cell population to change to a functional cell type.

The substantially homogenous cell population which co-express CD49c and CD90 do not, after between about 20 population doublings to about 50 population doublings, substantially express at least one cell senescent marker selected from a group consisting of P21 and P53. A senescent marker would be any marker associated with senescence or aging in a cell (e.g., P21, P53). The senescent marker can be a cytoplasmic, nuclear or cell surface marker.

In one embodiment, the cells of the invention undergo about 20 population doublings and still co-express CD49c and CD90 but do not substantially express at least one cell senescent marker selected from a group consisting of P21 and P53. In another embodiment, the cells of the invention undergo about 30 population doubles and still co-express CD49c and CD90 but do not substantially express at least one cell senescent marker selected from a group consisting of P21 and P53. In yet another embodiment, the cells of the invention undergo about 40 population doublings and still co-express CD49c and CD90 but do not substantially express at least one cell senescent marker selected from a group consisting of P21 and P53. In still another embodiment, the cells of the invention undergo about 50 population doublings and still co-express CD49c and CD90 but do not substantially express at least one cell senescent marker selected from a group consisting of P21 and P53. One of skill in the art would be able to determine when a cell has undergone a population doubling (Freshney, R. I. "Culture of Animal Cells: A Manual of Basic Techniques" New York, Wiley-Liss (1994)) and be able to determine whether the cell populations co-express CD49c and CD90 and do not substantially express at least one cell senescent marker selected from a group consisting of P21 and P53 employing established techniques (e.g., flow cytometry, quantitative PCR).

The substantially homogenous cell population of the invention which co-express CD49c and CD90 can further include expression of P21 or P53 after between about 20 to about 50 population doublings of the cells. Expression of a senescent marker (e.g., P21, P53) is a relative expression of the senescent marker (e.g., relative to 18s rRNA GAPDH (Glyceraldehyde-3-phosphate dehydrogenase), actin). "Relative expression," as used herein, is expression (e.g., nucleic acid, protein) of a molecule of interest (e.g., CD49c, CD90, telomerase, CBFA1, BSP, BDNF, IL-6, MCP-1) with respect to expression of a standard or reference marker (e.g. 18s rRNA, actin, GFAP). In a preferred embodiment, expression of P53 is a relative expression of up to about 3000 transcripts of P53 (e.g., 0, 100, 1000, 1500, 2000) per $10^6$ transcripts of an 18s rRNA and expression of P21 is a relative expression of up to about 20,000 transcripts of P21 per $10^6$ transcripts of an 18s rRNA.

In one embodiment, the expression of p53 is about 3000 transcripts of p53 per $10^6$ transcripts of an 18s rRNA. In another embodiment, the expression of p53 is about 2000 transcripts of p53 per $10^6$ transcripts of an 18s rRNA. In yet another embodiment, the expression of p53 is about 1000 transcripts of p53 per $10^6$ transcripts of an 18s rRNA.

In another embodiment, the expression of p21 is up to about 20,000 transcripts of p21 (e.g., 0, 100, 1000, 5000, 10000, 15000, 20000) per $10^6$ transcripts of an 18s rRNA. In still another embodiment, the expression of p21 is about 15,000 transcripts of p21 per $10^6$ transcripts of an 18s rRNA. In yet another embodiment, the expression of p21 is about 500 transcripts of p21 per $10^6$ transcripts of an 18s rRNA.

In one embodiment, the expression of a bone lineage marker core binding factor 1 (CBFA1) (Otto, F. et al., Cell 89(5) 765-771 (1997)) is about 5000 transcripts of the bone lineage marker per $10^6$ transcripts of an 18s rRNA. In another embodiment, the expression of the bone lineage marker CBFA1 is about 3000 transcripts of the bone lineage marker per $10^6$ transcripts of an 18s rRNA. In still another embodiment, the expression of the bone lineage marker CBFA1 is about 1000 transcripts of the bone lineage marker per $10^6$ transcripts of an 18s rRNA.

The substantially homogenous cell population of the invention can be a cell population from any human tissue (e.g., bone marrow, fat, skin, placenta, muscle, umbilical cord blood). In a preferred embodiment, the substantially homogeneous cell population is derived from bone marrow cells (e.g., human bone marrow stromal cells). Cells of the invention can be referred to as "derived" from any human tissue. Cells derived from tissues can be obtained, for example, by lysis of the source of the cells (e.g., bone marrow cells). For example, bone marrow stromal cells are derived from whole bone marrow aspirates after ammonium chloride lysis of the bone marrow aspirates. The ammonium chloride removes red blood cells from the aspirates and the resulting cell pellet is employed to generate the substantially homogenous cell population which co-express CD49c and CD90 cells of the invention. Alternatively, the bone marrow can be processed (e.g., fractionated by density gradient centrifugation, $NH_2Cl$ lysis, fluorescent activated sorting or magnetic sorting) to derive the cell populations of the invention. For example, the bone marrow aspirates or lysed bone marrow cells are passed through a density gradient to separate the cells of the invention from cellular debris as a result of lysis. Alternatively, or additionally, the bone marrow aspirates or lysed bone marrow cells can form a density gradient.

Whole bone marrow aspirates are obtained from a human and cultured in contact with a solid phase. Alternatively, or additionally, the whole bone marrow aspirate can be processed to yield a mononuclear cell fraction which is the cultured in contact with a solid phase. The solid phase can be plastic (e.g., tissue culture treated plastics).

The mononuclear cell fraction can be obtained from a whole bone marrow aspirate on a density gradient by established procedures. Alternatively, the mononuclear cell fraction is obtained by lysis of the red blood cells contained in the bone marrow aspirate. The lysis is done by mixing the bone marrow aspirate with ammonium chloride.

Human bone marrow cells are obtained from healthy human donors by aspirations of the iliac crest and bone marrow stromal cell populations obtained employing well established techniques. For example, substantially homogenous cell populations which co-express CD49c and CD90 are obtained from human iliac crest bone marrow aspirates and processed to mononuclear cell fractions from which bone marrow stromal cells are selectively propagated in vitro based upon their propensity to attach to plastic and divide in response to defined cell culture medium. The plastic-adherent cells are optimally grown at a cell concentration that encourages virtually only the self-renewing cells, referred to as colony-forming unit fibroblast-like cells (Cfu-f), to proliferate. The Cfu-f-derived cells are analyzed for cells which co-express CD49c and CD90 and sub-cultured to produce a substantially homogenous cell population which co-express CD49c and CD90.

The bone marrow aspirate, or a cellular fraction of the bone marrow aspirate, is cultured in contact with a solid phase and an intermediate cell population is isolated from the resulting cell culture based on their propensity to adhere to the solid phase. Bone marrow aspirates, or a cellular fraction of the aspirate, are cultured at a dissolved oxygen concentration of less than about 20%, preferably between about 1% to about 10%, and most preferably from between about 2% oxygen to about 7% oxygen. In a preferred embodiment, the dissolved oxygen concentration is about 5% oxygen. The resulting adherent cell population is expanded to yield a substantially homogeneous cell population which co-express CD49c and CD90.

Bone marrow cell expansion is conducted with a seeding density of less than about 2500 cell/cm$^2$, preferably less than about 1000 cells/cm$^2$, and most preferably less than about 100 cells/cm$^2$. In a particular embodiment, the initial cell density in the expansion step is between about 30 cells/cm$^2$ to about 50 cells/cm$^2$. A seeding density would be the number of adherent cells per cm$^2$ obtained from mononuclear bone marrow cells.

Standard media preparations can be used to culture the bone marrow cells. For example, the media can be minimum essential medium-alpha modification supplemented with 4 mM L-glutamine and 0 to 10% lot selected fetal bovine serum (FSB), preferably about 10% FSB. The culturing step can be conducted for any reasonable period, for example, between about 3 to about 25 days and most preferably between about 3 to about 15 days.

An intermediate cell population is isolated from the cell culture describe above based on its propensity to adhere to the solid phase. The intermediate cell population is grown at a cell concentration that encourages virtually only the self-renewing cells, referred to herein as colony-forming unit fibroblast-like cells (Cfu-f), to proliferate. The Cfu-f-derived cells are sub-cultured under defined conditions to produce a substantially homogeneous population of cells (Example 1). According to the invention, the expansion yields a substantially homogeneous cell population which co-express CD 49 and CD 90.

In another embodiment, the substantially homogenous cell population does not express CD34 and/or CD45. The presence or absence of CD34 and CD45 can be detected on bone marrow mononuclear cells which co-express CD49c and CD90 using routine methods including, for example, antigen-specific ELISA assays, quantitative PCR, or flow cytometry.

Cells which co-express CD49c and CD90, but do not express either or both CD34 and/or CD45, are propagated in culture and stored until use in the methods of the invention.

In yet another embodiment, the substantially homogenous population of cells co-expressing CD49c and CD90 express a trophic factor selected from the group consisting of brain-derived neurotrophic factor (BDNF) (Barde, Y. A., et al. *EMBO J.*, 1(5):549-553 (1982)), nerve growth factor (NGF) (Levi-Montalcini, R., Arch Biol 76(2):387-417 (1965)), neurotrophin-3 (NT-3) (Mohn, A., et al., *Nature* 344:339-341 (1990)), interleukin-6 (IL-6) (Barton, B. E., *Clin. Immumol. Immunopathol.* 85(1):16-20 (1997)), interleukin-7 (IL-7), interleukin-11 (IL-11), stem cell factor (SCF), macrophage chemoattractin protein-1 (MCP-1), matrix metalloproteinase-9 (MMP-9) and Cystatin-C.

Expression of BDNF, NGF, NT-3, IL-6, IL-7, IL-11, SCF, MCP-1, MMP-9 and Cystatin-C in substantially homogenous populations of cells co-expressing CD49c and CD90 can be augmented by a variety of techniques, including ex vivo cultivation of the cells in chemically defined medium.

In yet another embodiment, the invention is a substantially homogenous cell population which co-express CD49c, CD90 and telomerase. Expression of telomerase is a relative expression, for example, a relative expression of greater than between about 1 transcript of telomerase per $10^6$ transcripts of an 18s rRNA and about 10 transcripts of telomerase per $10^6$ transcripts of an 18s rRNA. In one embodiment, expression of telomerase is about 1 transcript of telomerase per $10^6$ transcripts of an 18s rRNA. In another embodiment, expression of telomerase is about 5 transcripts of telomerase per $10^6$ transcripts of an 18s rRNA. In yet another embodiment, expression of telomerase is about 10 transcripts of telomerase per $10^6$ transcripts of an 18s rRNA.

The cell population which co-express CD49c, CD90 and telomerase has a doubling time of less than about 144 hours, less than about 72 hours or less than about 48 hours.

The cell population which co-express CD49c, CD90 and telomerase has the potential to differentiate into a preselected phenotypes (e.g., a chondrocyte, an astrocyte, an oligodendrocyte, a neuron, osteocyte, osteoblast, osteoclast, a cardiomyocyte, a pancreatic islet cell, a skeletal muscle, a smooth muscle, a hepatocyte and a retinal ganglial cell).

The cell population which co-express CD49c, CD90 and telomerase can further include expression of P21 or P53 after between about 20 to about 50 population doublings of the cells (e.g., 20, 30, 40 or 50 population doublings). Expression of P53 is a relative expression of up to about 3000 transcripts of P53 per $10^6$ transcripts of an 18s rRNA (e.g, 3000, 2000 or 1000 transcripts of P53 per $10^6$ transcripts of an 18s rRNA). Expression of P21 is a relative expression of up to about 20,000 transcripts of P21 per $10^6$ transcripts of an 18s rRNA (e.g., 20000, 15000 or 5000 transcripts of P21 per $10^6$ transcripts of an 18s rRNA).

In another embodiment, the cell population which co-express CD49c, CD90 and telomerase does not express CD34 and/or CD45. In yet another embodiment, the cell population which co-express CD49c, CD90 and telomerase express at least one trophic factor selected from the group consisting of BDNF, IL-6 and MCP-1.

In still another embodiment, the invention includes a method of making a substantially homogenous cell population which co-express CD49c and CD90 comprising culturing a source of the cell population (e.g., human bone marrow cells) and selecting from the cultured source of the cell population, cells which co-express CD49c and CD90. In one embodiment, the source of the cell population is cultured under a low oxygen condition (e.g., less than atmospheric).

"Low oxygen condition," as used herein, refers to a concentration (e.g., percent of oxygen based on volume, weight or molarity) which is less than atmospheric oxygen.

In still another embodiment, the invention includes a method of making a substantially homogenous cell population which co-express CD49c, CD90 and telomerase comprising culturing a source of the cell population (e.g., human bone marrow cells) and selecting from the cultured source of the cell population, cells which co-express CD49c, CD90 and telomerase.

In a further embodiment, the invention includes a method of making a substantially homogenous cell population which co-express CD49c and CD90 but does not express bone salioprotein comprising culturing a source of the cell population and selecting from the cultured source of the cell population, cells which co-express CD49c, CD90 and a bone lineage marker.

In a preferred embodiment, the low oxygen condition is an oxygen concentration less than about 15% oxygen, and more preferably an oxygen concentration less than about 10%, and most preferably an oxygen concentration of about 5% oxygen. In another embodiment, the source of the cell population is cultured at a seeding density of less than about 100 cells/cm$^2$ (e.g., 95, 90, 80, 50, 30, 25 cells/cm$^2$) under low oxygen conditions (e.g., less than atmospheric, 5% oxygen).

In an additional embodiment, the invention includes a method of making a substantially homogenous cell population which co-express CD49c and CD90 comprising culturing a source of the cell population (e.g., human bone marrow cells) and selecting from the cultured source of the cell population, cells which co-express CD40c and CD90 by culturing the source of the cell population under low oxidative stress (e.g., glutathione, Vitamin C, Catalase, Vitamin E, N-Acetylacysteine). "Low oxidative stress," as used herein, refers to conditions of no or minimal free radical damage to the cultured cells.

The method of making a substantially homogenous population of cells which co-express CD49c and CD90; co-express CD49c, CD90 and telomerase; or co-express CD49c, CD90 but does not express bone salioprotein (BSP), can further include lysing the source of the cell population (e.g., bone marrow aspirates) prior to culturing the source of the cell population. For example, lysis of a bone marrow aspirate can result in the lysis of hematopoietic cells leaving the non-hematopoietic cells un-lysed. Additionally, or alternatively, the method can further include fractionating (e.g., by passage through or formation of a density gradient, by NH$_2$Cl lysis) the source of the cell population (e.g., bone marrow aspirates) prior to culturing the source of the cell population.

The cells made by the method of the invention can also express at least one trophic factor (e.g., BDNF, NGF, NT-3, IL-6, IL-7, IL-11, SCF, MCP-1, MMP-9 and Cystatin-C). In another embodiment, the substantially homogenous population of cells which co-express CD49c and CD90; co-express CD49c, CD90 and telomerase; co-express CD49c, CD90 but does not express bone saliprotein, made by the method of the invention do not express CD34 and/or CD45.

In still another embodiment, the invention is a method of treating a human suffering from a degenerative or acute injury condition, comprising the step of administering to the human a substantially homogenous cell population which co-express CD49c and CD90. The cells used to treat the human suffering from a degenerative or acute injury condition can also not express CD34 and/or CD45.

Degenerative disease is a disease in which the decline (e.g., function, structure, biochemistry) of particular cell type (e.g., neuronal, muscle, connective, epithelial) results in an adverse clinical condition. For example, Parkinson's disease is a degenerative disease in the central nervous system (e.g., basal ganglia) which is characterized by rhythmical muscular tremors, rigidity of movement, festination, droopy posture and masklike facies. Degenerative diseases that can be treated with the substantially homogenous cell populations of the invention which co-express CD49c and CD90 can be, for example, Parkinson's disease, Huntington's disease, Alzheimer's disease, amyotrophic lateral sclerosis, congenital heart failure, cardiomyopathy, ataxias, and spinal muscular dystrophy.

An acute injury condition is a condition in which an event or multiple events results in an adverse clinical condition. The event which results in the acute injury condition can be an external event such as blunt force or compression or an internal event such as sudden ischemia (e.g., stroke or heart attack). Acute injury conditions that can be treated with the substantially homogenous cell populations of the invention which co-express CD49c and CD90; which co-express CD49c, CD90 and telomerase; which co-express CD49c and CD90, but does not express bone sialoprotein (BSP), can be, for example, spinal cord injury, traumatic brain injury, myocardial infarction and stroke.

In a further embodiment, the invention includes a method of treating a human suffering from a cardiac condition, comprising the step of administering to the human a substantially homogenous cell population which co-express CD49c and CD90. A cardiac condition is a disease of the heart. The disease of the heart can be a disease of the cardiac muscle, connective tissue of vessels of the heart. The cells used to treat the human suffering from a cardiac condition can also not express CD34 and/or CD45. A cardiac condition that can be treated by the cells of the invention can be, for example, myocardial infarction, myocarditis, vascular heart disease, cardiomyopathy, congenital heart disease, eschemic heart disease, heart transplant and pre-transplantation bridge.

An additional embodiment of the invention includes a method of treating a human suffering from a neurological condition, comprising the step of administering to the human a substantially homogenous cell population which co-express CD49c and CD90; co-express CD49c, CD90 and telomerase; CD49c, CD90 and a bone lineage marker. "A neurological condition," as used herein, refers to any state of the nervous system (central or peripheral nervous system) which deviates in any manner from a normal nervous system or nervous system of a mammal (e.g., human) not affected by a neurological condition. The neurological condition can be a condition of the central (brain or spinal cord) or peripheral nervous system. The neurological condition can be, for example, the result or consequence of a disease (e.g., amyotrophic lateral sclerosis, Parkinson's Disease, Fabry Disease), acute injury condition (e.g., stroke, brain injury, spinal cord injury) or a combination of disease and acute injury condition. Other neurological conditions which can be treated with the substantially homogenous population of cells of the invention which co-express CD49c and CD90 include, for example, metachromatic distropy, adrenal leukodystrophy, Canavan disease, Pelizaeus Merzbacher, Nieman-pick and a brain tumor.

In still another embodiment, the invention includes a method of treating a human suffering from a neurological condition, comprising culturing (e.g., low oxygen conditions; oxygen conditions less than atmospheric; about 5% oxygen) a source of a cell population (e.g., bone marrow, fat, cord blood, skin) and selecting from the cultured source of the cell population, a population of cells which co-express CD49c and CD90. The selected population of cells which co-express CD49c and CD90 are administered to the human.

In one embodiment, the substantially homogenous population of cells which are administered to the human co-express CD49c and CD90 and lack CD34 and/or CD45. In another embodiment, the substantially homogenous population of cells which are administered to the human co-express CD49c, CD90 and telomerase. In yet another embodiment, the substantially homogenous population of cells which are administered to the human co-express CD49c and CD90 or co-express CD49c, CD90 and telomerase and express at least three trophic factors selected from the group consisting of BDNF, NGF, NT-3, IL-6, IL-7, IL-11, SCF, MCP-1, MMP-9 and Cystatin-C (e.g., BDNF, IL-6 and MCP-1).

The synthesis and secretion of cytokines and trophic factors from the substantially homogenous population of cells of the invention can protect surrounding cells near or distant from the site of transplantation from further damage as a consequence of the degenerative, acute injury or neurological condition. The synthesis and secretion of cytokines and trophic factors from the substantially homogenous population of cells of the invention can also, or alternatively, promote regeneration of cells and tissues of the host (e.g., human suffering from a acute injury, neurological, cardiac or degenerative condition) treated with the substantially homogenous population cells of the invention which co-express CD49c and CD90 or co-express CD49c, CD90 and telomerase.

The substantially homogenous population of cells which co-express CD49c and CD90 or which co-express CD49c, CD90 and telomerase when administered to the human may respond to cellular signaling and physiological cues in the human and migrate to the area of injury or trauma and, therefore, be used as delivery vehicles for proteins and genes of interest.

In another embodiment, the invention is a method of treating a human suffering from a neurological condition (e.g., spinal cord injury, an amyotrophic lateral sclerosis, a Parkinson's Disease, a stroke, a traumatic brain injury, a Fabry Disease condition, metachromatic distropy, adrenal leukodystrophy, Canavan disease, Pelizaeus Merzbacher, Nieman-pick, a brain tumor) by culturing a source of a cell population at a seeding density of less than about 100 cells/cm² under a low oxygen condition; selecting from the cultured source of the cell population, a population of cells which co-express CD49c and CD90; and administering the population of cells which co-express CD49c and CD90 to the human.

The transplantation of the substantially homogenous cell population of the invention into a patient suffering from a neurological condition may result in the differentiation of the cells of the invention into cells which normally function in the nervous tissue affected in the human with the neurological condition thereby treating a myriad of neurological conditions including, for example, Parkinson's disease, ALS, spinal cord injury, brain tumors, stroke. Similarly, the homogenous cell population of the invention can be used to treat a human suffering from a non-neurological condition such as a burn, heart disease, diabetes, osteoarthritis and rheumatoid arthritis.

The cell populations of the invention may have the capacity to respond to intrinsic signals (e.g., at the sites of transplantation or when incorporated into tissues and organs) and exogenous cues to differentiate into numerous cell types (e.g., neuronal, glial, astrocytes, oligodendrocystes) in the human. The cell populations of the invention can provide a readily available source of cells for use in treating humans. The cell populations of the invention can be readily isolated from adult or embryonic tissues, proliferate at high rates, have large expansion potential, can be stable for long periods of time, can be responsive to exogenous signals and can produce sufficient therapeutic quantities of molecules of interest.

Accordingly, another embodiment of the invention is a method of making a committed progenitor cell by culturing (e.g., under a low oxygen condition, 5% oxygen) a source of a cell population (e.g., bone marrow cells, human bone marrow cells, fat, cord blood, skin) and selecting from the cultured source of the cell population cells which co-express CD49c and CD90. The population of cells which co-express CD49c and CD90 are modified to become committed progenitor cells. The selection of cells from the cultured source of the cell population cells which co-express CD49c and CD90 is achieved by a low oxygen condition (e.g., oxygen below atmospheric oxygen, 5% oxygen).

"Committed progenitor cell," as used herein, refers to a precursor cell obtained from a source (e.g., human bone marrow, fat, cord blood, skin) which develops into a cell for a particular purpose. A committed progenitor cell can be, for example, a CD49c/CD90 cellderived from human bone marrow which can differentiate or develop into, for example, a neuron, glial, astrocyte or oligodendrocyte cell.

In another embodiment, the invention is a method of treating a human suffering from a neurological condition by culturing a source of a cell population (e.g., bone marrow aspirates) and selecting (e.g., by a low oxygen culture condition) from the cultured source of the cell population, cells which co-express CD49c and CD90; co-express CD49c, CD90 and telomerase; or co-express CD49c, CD90 and a bone lineage marker. The selected cells which co-express, for example, CD49c and CD90 are modified to become a committed progenitor cell and administered to a human with a neurological condition (e.g., a spinal cord injury, an amyotrophic lateral sclerosis, a Parkinson's Disease, a stroke, a traumatic brain injury, a Fabry Disease condition, metachromatic distropy, adrenal leukodystrophy, Canavan disease, Pelizaeus Merzbacher, Nieman-pick and a brain tumor).

Techniques to assess whether a cell of the substantially homogenous population of cells of the invention which co-express CD49c and CD90; co-express CD49c, CD90 and telomerase; or CD49c, CD90 but does not express bone salioprotein (BSP) become committed progenitor cells are within the expertise of one of skill in the art. For example, cells which co-express CD49c and CD90 can be cultured, selected and modified to produce and express the neuronal cell markers, such as noggin, musashi or Sox2, which would indicate that the cells are committed neuronal progenitors cells. Techniques to determine whether a cell has become a committed progenitor cell are well-established and known to one of skill in the art (e.g., quantitative PCR, flow cytometry).

Cells which co-express CD49c and CD90 can be selected from a source of a cell population for making the committed progenitor cells. Selected cells which co-express CD49c and CD90 (also referred to herein as "selected cells") can be, for example, modified to become committed progenitor cells by culturing the selected cells in:

1. DMEM/F12/ITS/2 mM Glutamine/BSA1 mg/ml;
2. DMEM/F12/ITS/2 mM Glutamine/BSA1 mg/ml/0.25 ng/ml IL-$\beta$;
3. DMEM/F12/ITS/2 mM Glutamine/BSA1 mg/ml/2 ng/ml TNF$\alpha$;
4. DMEM/F12/ITS/2 mM Glutamine/BSA1 mg/ml/100 ng/ml NT-3;
5. DMEM/F12/ITS/2 mM Glutamine/BSA1 mg/ml/100 ng/ml Noggin;
6. DMEM/F12/ITS/2 mM Glutamine/BSA1 mg/ml/100 ng/ml GDNF;

7. DMEM/F12/ITS/2 mM Glutamine/BSA1 mg/ml/20 ng/ml/bFGF;
8. DMEM/F12/ITS/2 mM Glutamine/BSA1 mg/ml/10 µM Forskolin;
9. DMEM/F12/ITS/2 mM Glutamine/BSA1 mg/ml/1 µM Bay K 8644; and/or
10. DMEM/F12/B27/2 mM Glutamine/BSA1 mg/ml.
11. MEM-Alpha/4 mM Glutamine/10% ser lot selected fetal bovine serum and 5 mM nifedipine Selected cells can be used directly from cultures or stored for future use (e.g., by freezing in liquid nitrogen).

In one embodiment, the committed progenitor cells of the invention do not express CD34 and/or CD45. In another embodiment, the committed progenitor cells of the invention express at least one trophic factor selected from the group consisting of BDNF, NGF, NT-3, IL-6, IL-7, IL-11, SCF, MCP-1, matrix metalloproteinase-9 (MMP-9) and Cystatin-C (e.g., BDNF, IL-6 and MCP-1).

In an additional embodiment, the invention is a method of treating a human suffering from a neurological condition, comprising culturing a source of a cell population (e.g., bone marrow, human bone marrow, fat, cord blood, skin) and selecting from the cultured source of the cell population cells which co-express CD49c and CD90. The selected cells are modified to become a committed progenitor cell. The committed progenitor cells are administered to a human.

In still another embodiment, the invention includes a pharmaceutical composition comprising a substantially homogeneous cell population which co-express CD49c and CD90 (e.g., between about $5 \times 10^5$ to $2 \times 10^6$ cells). In one embodiment, the pharmaceutical composition has at least about $10^5$ substantially homogeneous cells which co-express CD49c and CD90. In another embodiment, the pharmaceutical composition has at least about $10^6$ substantially homogeneous cells which co-express CD49c and CD90. The cells comprising the pharmaceutical composition can also not express CD34 and/or CD45 and/or can express at least one trophic factor selected from the group consisting of BDNF, NGF, NT-3, IL-6, IL-7, IL-11, SCF, MCP-1, matrix metalloproteinase-9 (MMP-9) and Cystatin-C.

In a further embodiment, the invention includes a pharmaceutical composition comprising a substantially homogeneous cell population which co-express CD49c, CD90 and telomerase.

The substantially homogenous cells of the invention which co-express CD49c and CD90; co-express CD49c, CD90 and telomerase; or co-express CD49c, CD90 but does not express BSP, can be administered to a human suffering from a neurological condition. A "therapeutically beneficial amount" of the substantially homogeneous population of cells of the invention is a quantity sufficient to enhance neuronal function in a subject having a neurological condition (e.g., spinal cord injury) to be clinically relevant.

The cells of the invention can be, for example, transplanted or placed in the central (e.g., brain or spinal cord) or peripheral nervous system. The site of placement in the nervous system for the cells of the invention is determined based on the particular neurological condition (e.g., direct injection into the lesioned spinal cord parenchyma, intra-thecal injection, or intravenous injection). For example, cells of the invention can be placed in or near the substantia nigra of patients suffering from Parkinson's disease. Similarly, cells of the invention can be placed in or near the spinal cord (e.g., cervical, thoracic, lumbar or sacral) of patients suffering from a spinal cord injury.

The cells of the invention can be placed or transplanted in cavities or spaces of the central or peripheral nervous system. For example, the cells of the invention can be placed in the ventricles of the brain, subarachoid space of the spinal cord, or vertebral canal of the spinal cord. One skilled in the art would be able to determine the manner (e.g., needle injection or placement, more invasive surgery) most suitable for placement of the cells depending upon the location of the neurological condition and the medical condition of the patient.

In addition, routes of administration of the cells of the invention, or when cells of the invention are admixed with pharmaceutical carriers, encompassed by the present invention include, for example, intramuscular, intravenous, intraarterial, intraperitoneal, subcutaneous routes or nasal administration.

The substantially homogenous cells of the invention which co-express CD49c and CD90 can be administered alone or as admixtures with conventional excipients, for example, pharmaceutically, or physiologically, acceptable organic, or inorganic carrier substances suitable for enteral or parenteral application which do not deleteriously react with the cells of the invention. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the cells of the invention.

When parenteral application is needed or desired, particularly suitable admixtures for the cells are injectable, sterile solutions, preferably oily or aqueous solutions, as well as suspensions, emulsions, or implants, including suppositories and soaking in GELFOAM®. In particular, carriers for parenteral administration include aqueous solutions of dextrose, saline, pure water, ethanol, glycerol, propylene glycol, peanut oil, sesame oil and polyoxyethylene-block polymers. Pharmaceutical admixtures suitable for use in the present invention are well-known to those of skill in the art and are described, for example, in Pharmaceutical Sciences (17th Ed., Mack Pub. Co., Easton, Pa.) and WO 96/05309 the teachings of both of which are hereby incorporated by reference.

The substantially homogeneous population of cells which co-express CD49c and CD90 can be used alone or in any combination when administered to a human suffering from a neurological condition. For example, steroids or pharmaceutical synthetic drugs can be co-adminstration with the cells of the invention. Likewise, treatment of spinal cord injury can include the administration/transplantation of the cells of the invention in a human whose spine has been physically stabilized.

The dosage and frequency (single or multiple doses) of the administration or transplantation of the cells to a human, including the actual number of cells transplanted into the human, can vary depending upon a variety of factors, including the particular condition being treated (e.g., neurological condition, cardiac condition, degenerative condition, acute injury) size, age, sex, health, body weight, body mass index, diet of the human, nature and extent of symptoms of the neurological condition being treated (e.g., early onset Parkinson's disease versus advanced Parkinson's disease; spinal cord trauma versus partial or complete severing of the spinal cord), kind of concurrent treatment (e.g., steroids), complications from the neurological condition, extent of tolerance to the treatment or other health-related problems.

Humans with a neurological condition can be treated for days (e.g., 30) with cells of the invention (e.g., about $10^6$ cells), by a several routes of administration (e.g., intrathecal, intravenous).

It is also envisioned that the methods of the invention can be employed to treat neurological conditions in mammals other than human mammals. For example, a non-human mammal in need of veterinary treatment, e.g., companion animals (e.g., dogs, cats), farm animals (e.g., cows, sheep, pigs, horses) and laboratory animals (e.g., rats, mice, guinea pigs).

The present invention is further illustrated by the following examples, which are not intended to be limiting in any way.

EXEMPLIFICATION

Example 1

Isolation of a Adherent as Colony Forming Units of Cells or "CFUs" from Bone Marrow Aspirates Following Red Blood Cell Lysis Bone marrow cells were aspirated from the iliac crest of healthy adult human volunteers. The red blood cell component of the aspirate was lysed by mixing the aspirate with an ammonium chloride buffer consisting of 155 mM ammonium chloride, 10 mM potassium bicarbonate and 0.1 mM EDTA (ethylenediaminetetraacetic acid), pH 7.2, at a 1:20 ratio of marrow aspirate to buffer. The resulting cell suspension was vortexed for 2 seconds, incubated for 2 minutes at ambient temperature and then centrifuged (10 minute at 500×g). The resulting mononuclear cell pellet was resuspended in complete medium and centrifuged (10 minutes at 500×g). Complete media is Minimal Essential Medium-alpha (Gibco BRL, Rockville, Md.) supplemented with 4 mM glutamine and 10% sera-lot selected fetal bovine serum (FBS, Gibco BRL, Rockville, Md.). The cell pellet was then re-suspended in the complete medium and centrifuged a second time (10 minutes at 500×g).

The resulting pellet was re-suspended in the complete medium and the number of viable cells was determined by trypan blue-exclusion. The mononuclear cell suspension was then seeded in tissue culture-treated T75 flask at a density of 50,000 cells/cm2 and incubated at 37° C. in an atmosphere consisting of 5% carbon dioxide, 5% oxygen, and 90% nitrogen/air. On the fifth day of culture, the non-adherent cells and conditioned media (also referred to herein as "spent media") were aspirated from the flasks and the adherent cells re-fed with fresh complete medium. The adherent colony forming units (CFUs) were expanded for an additional 3-5 days.

The generation of CFUs was monitored in 6-well plates concurrently initiated under identical conditions to the T75 flasks. The spent medium was removed from the 6-well plates and the adherent cells were fixed for 5 minutes in 100% methanol, and then stained with methylene blue to visualize the CFUs. An initial seeding density of 75,000 cells/cm$^2$ efficiently generated CFUs. After processing the bone marrow aspirate by either FICOLL® density gradient separation or ammonium chloride lysis, CFU efficiency was dramatically affected by oxygen concentration.

After 7 days in culture, the purity (percentage of cells which co-express CD49c and CD90) of the CFUs generated was determined by flow cytometry. T75 flasks were washed twice with Hank's Balanced Salt Solution (HBSS; CellGro Technologies) and treated with 0.1% Trypsin/1 mM EDTA solution (Life Technologies) for 10 minutes at 37° C. Cultures were removed from incubator and 10 mL of complete medium was added. Cells were triturated from the flask, transferred to a 50 mL centrifuge tube and centrifuged (500×g for 5 minutes). The resulting pellet was resuspended in 10 mL of HBSS.

Figure 1B:
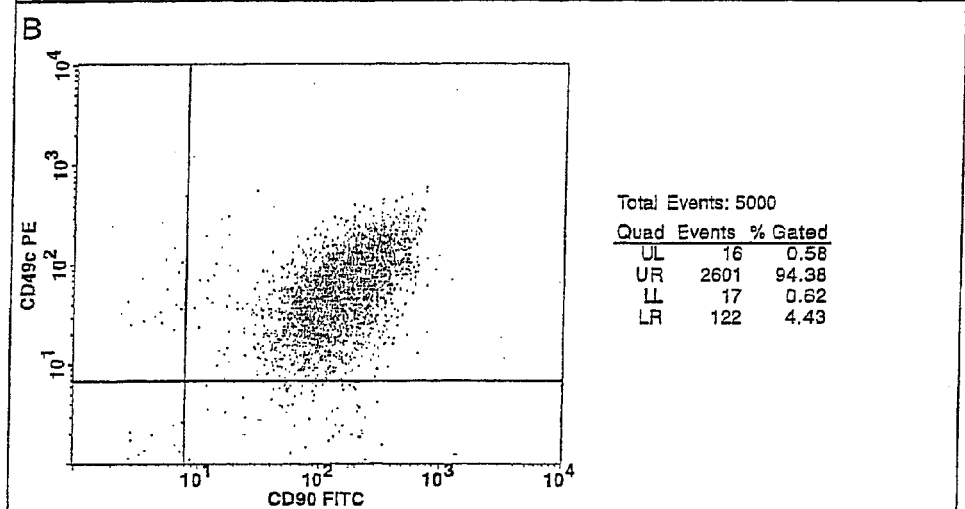

Resuspended cells (approximately $10^6$) were aliquoted into 12×75 mm Flow Cytometry tubes and repelleted at 500×g for 5 minutes. The HBSS was removed and 25 mL of the following antibodies (all obtained from Becton Dickenson), alone or in combination, were placed into each tube: mouse IgG1k-FITC or -PE (clone MOPC-21) CD49c-PE (cl. C3II.1), CD90-FITC (cl. 5E10), CD45-FITC or -PE (cl. HI30). Tubes were gently vortexed and incubated for 30 minutes at 4° C. Cells were then washed in HBSS/1% bovine serum albumin, centrifuged (30 min, 4° C.) and the resulting cellular pellet fixed by the addition of 250 microliters of 2% paraformaldhyde/HBSS. Flow cytometric analysis was performed employing a Becton-Dickenson FACSVantage SE cytometer and analyzed using CELLQUEST® software. FIG. 1 depicts results representing data collected from 2,500-10,000 events per panel. After compensation for non-specific antibody staining using mouse IgG1 isotype controls, cellular expression of CD45, CD49c and CD90 in the cultured bone marrow cells was assessed. The adherent population derived from mononuclear cells initially purified using ammonium chloride lysis contained approximately 70% CD49c positive cells at a similar stage of culture (FIG. 1A). The majority of cells that did not express CD49c were positive for expression of hematopoetic/myeloid lineage marker CD45 (FIG. 1A, LR quadrant), demonstrating that the CD49c positive cell population derived from human bone marrow isolated was not directly related to known hematopoietic precursors. More than 94% of the adherent population was CD90 and CD49c positive (FIG. 1B).

Example 2

Isolation of a Adherent CFUs from Bone Marrow Aspirates Following Density Separation Bone marrow cells were aspirated from the iliac crest of healthy adult human volunteers. The bone marrow aspirate was diluted with calcium and magnesium free phosphate buffered saline (PBS) to achieve a mononuclear cell concentration of $7 \times 10^6$ cells/mL and overlaid onto an equal volume of Histopaque® 1.119 (Sigma, St. Louis, Mo.) and centrifuged (30 min at 700×g). The resulting mononuclear cell fraction was transferred to a clean centrifuge tube containing PBS and centrifuged (10 minutes at 500×g). The cell pellet was re-suspended in PBS and centrifuged (10 minutes at 500×g). The supernatant was aspirated from the cell pellet and the cells re-suspended in complete media.

The number of viable cells in the resulting cell suspension was determined by trypan blue-exclusion. The cell suspension was then seeded in tissue culture-treated T75 flasks at a density of 50,000 cells/cm2 and incubated at 37° C. in an atmosphere of 5% carbon dioxide, 5% oxygen and 90% nitrogen/air. On the fifth day of culture, the non-adherent cells and conditioned media (also referred to herein as "spent media") was aspirated from the flasks and the adherent cells re-fed with fresh complete medium. The adherent CFUs were expanded for an additional 3-5 days.

Figure 2A:
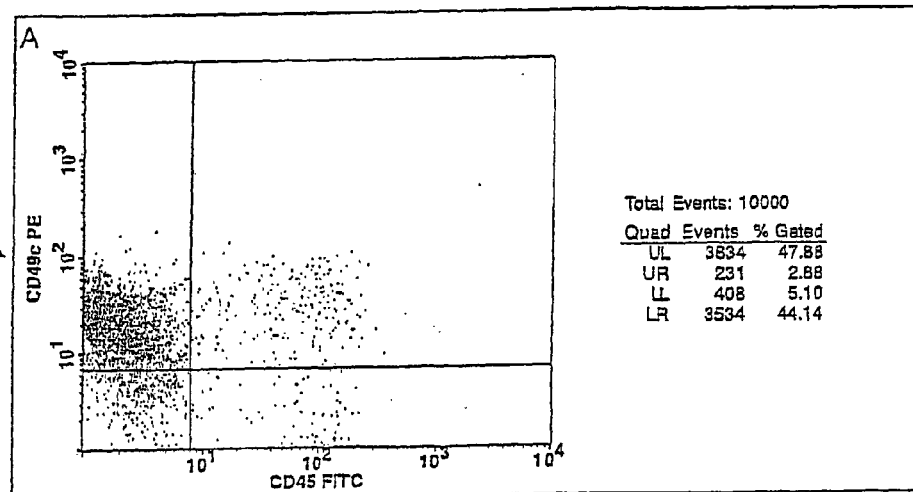
FIGS. 2A, 2B, and 2C illustrate the flow cytometric analysis of cell populations in the Master and Working Cell Banks generated from a bone marrow aspirate following density separation.
Figure 2B:
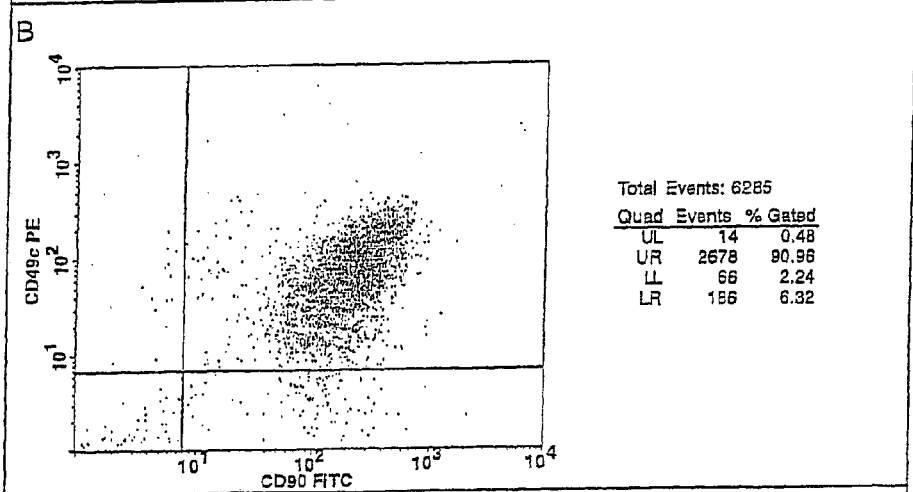

Cytometry analysis of the CFU generated showed that approximately 50% of the adherent population expressed the marker CD49c at 7 days in vitro (FIG. 2A, sum of UL and UR quadrants). The majority of cells that did not express CD49c were positive for expression of hematopoetic/myeloid lineage marker CD45 (FIG. 2A, LR quadrant), demonstrating that the CD49c positive cell population derived from human bone marrow isolated by this procedure was not directly related to known hematopoietic precursors. More than 91% of the adherent population was CD90 and CD49c positive (FIG. 2B).

Example 3

Production of Primary and Master Cell Banks from CFUs

After 7-10 days in culture, the CFUs generated using the methods described in Example 1 were removed from the T75 flasks with a 0.25% trypsin/1 mM EDTA solution (Life Technologies). After 10 minutes at 37° C., the trypsin was inactivated with 10 mL of complete medium. The cells were washed once with HBSS and re-suspended in Glycerol Cell Freezing Medium® (Sigma Chemical Co.). Aliquots (referred to herein as "the Primary Cell Bank") of the suspension consisting of $4.0 \times 10^5$ cells/vial were cooled with liquid nitrogen vapor at 1° C./minute using a CryoMed (Forma) controlled rate freezer and the stored in a Cryo Plus liquid nitrogen storage tank (Forma).

An aliquot of cells was removed from the Primary Cell Bank and cultured at a density of 30 cells/cm$^2$ in 500 cm$^2$ tissue culture-treated plates (Corning) in complete medium and incubated at 37° C. in an atmosphere consisting of 5% carbon dioxide, 5% oxygen, and 90% nitrogen/air. After two weeks of culture, cells were removed from the plates with trypsin and were cryopreserved at $4.0 \times 10^5$ cells/vial (referred to herein as "the Master Cell Bank").

Figure 1C:
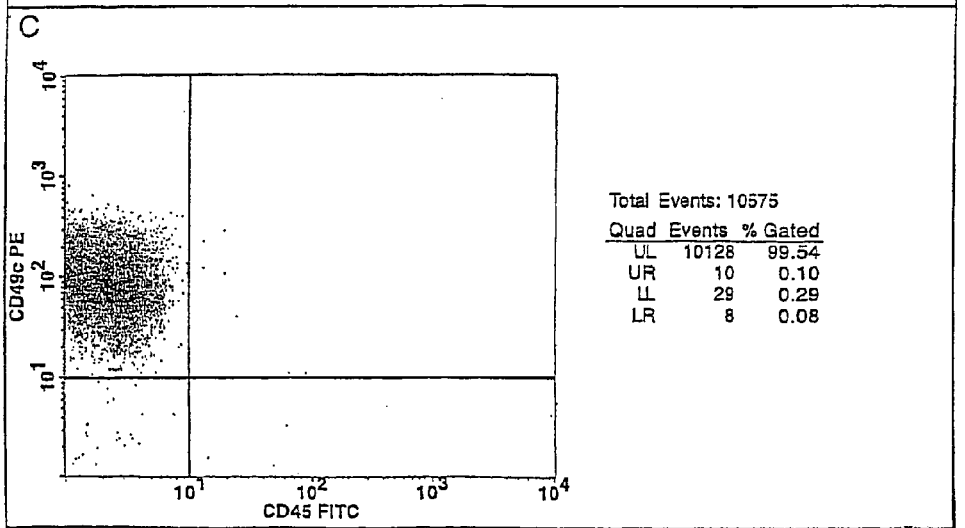

The purity of the cells (percentage of cells which co-express CD49c/CD90) in the Master Cell Bank was determined by flow cytometry using the same method as above. The vast majority (>98%) of the resulting population expressed CD90 (FIG. 1C) and virtually lacked any expression of the myeloid-related marker CD45 (FIG. 1C, LR quadrant). Thus, the expansion procedure as described herein produces a substantially homogenous population of adherent cells which co-express CD49c and CD90 and lack significant expression of the marker CD45.

Figure 2C:
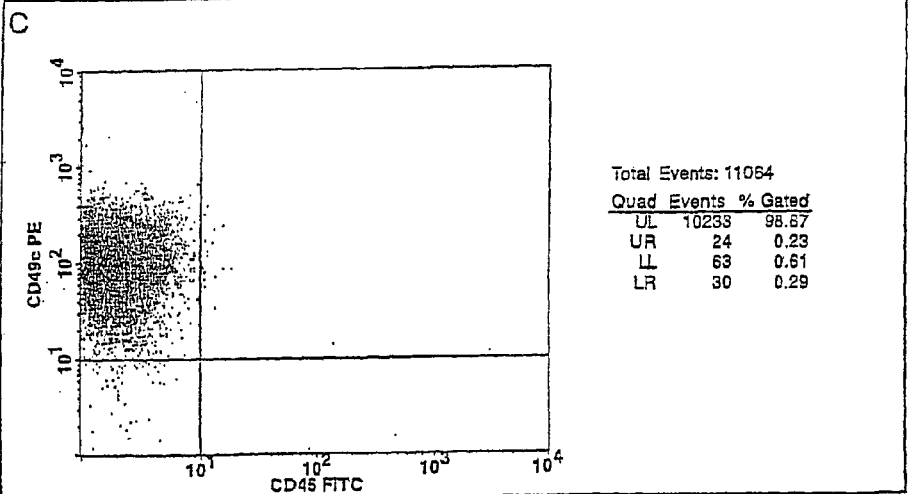

Similarly, the master cell bank generated from the CFU derived using method of Example 2 showed that the majority of cells (>98.8%) of the resulting cell population expressed CD90 (FIG. 2C) and virtually lacked any expression of the myeloid-related marker CD45 (FIG. 2C, LR quadrant). Thus, the expansion procedure as described herein generates a substantially homogenous population of adherent cells which co-express CD49c and CD90 and lack significant expression of the marker CD45.

Example 4

Expansion Capability of the Cell Population which Co-Express CD49c and CD90

A Primary Cell Bank of CFUs was derived from 25 mLs of bone marrow aspirate and stored as frozen aliquots using the methods of Examples 1 and 2. An aliquot was thawed, expanded and frozen to generate the Master Cell Bank as described in Example 3. An aliquot of cells was removed from the Master Cell Bank and cultured at a density of 30 cells/cm$^2$ in 500 cm$^2$ tissue culture-treated plates (Corning) in complete medium and incubated at 37° C. in an atmosphere consisting of 5% carbon dioxide, 5% oxygen, and 90% nitrogen/air. After two weeks of culture, cells were removed from the plates with trypsin and cryopreserved at $2\text{-}10 \times 10^6$ cells/vial.

The process was repeated in succession to produce additional Cell Banks of cells which co-express CD49c and CD90.

Figure 3:
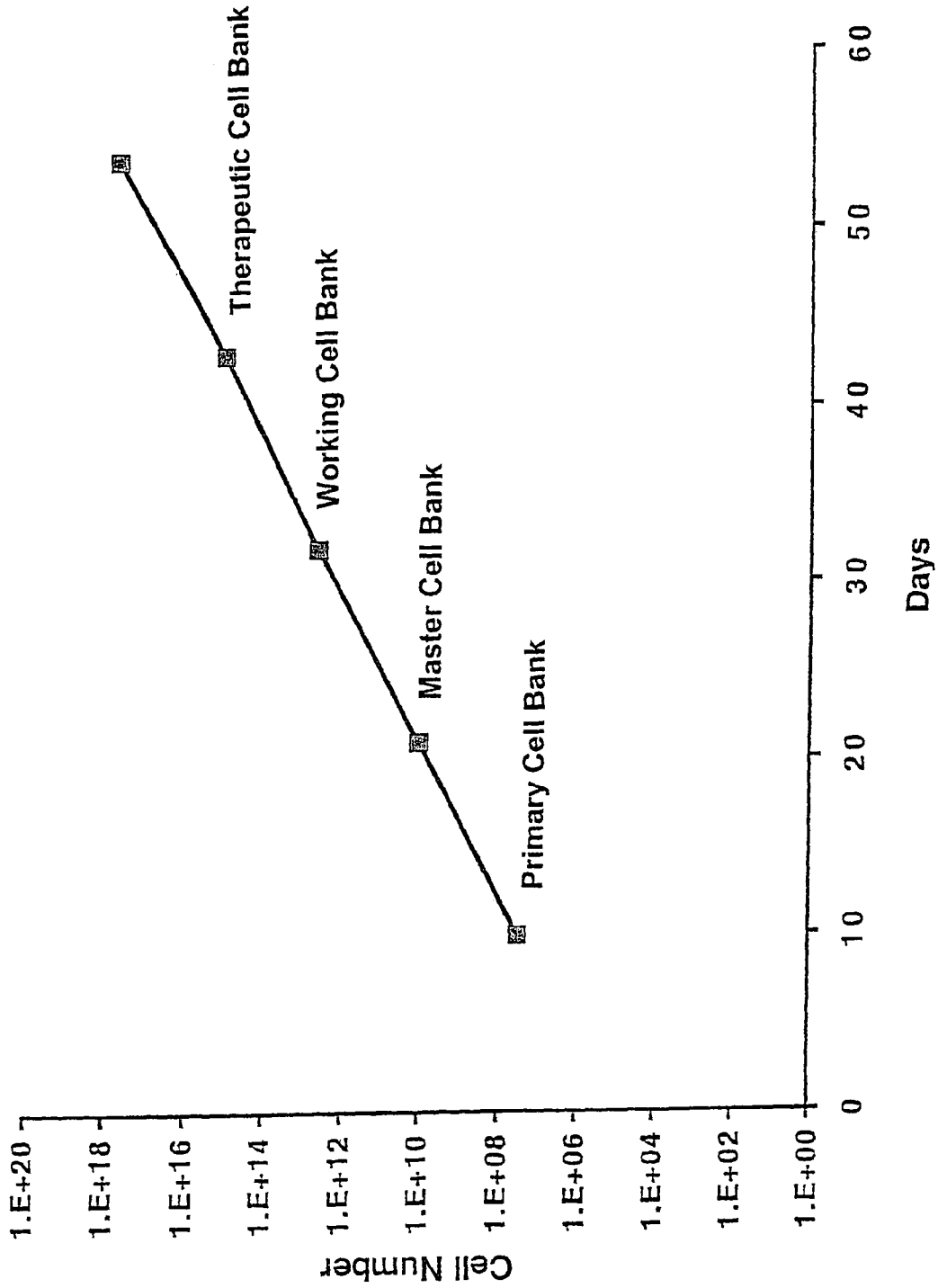
FIG. 3 illustrates the yield (Cell Number) of cells that co-express CD49c and CD90 cells during ex vivo expansion of a Primary Cell Bank of colony forming units (CFUs) derived from human bone marrow aspirates.
Figure 4:
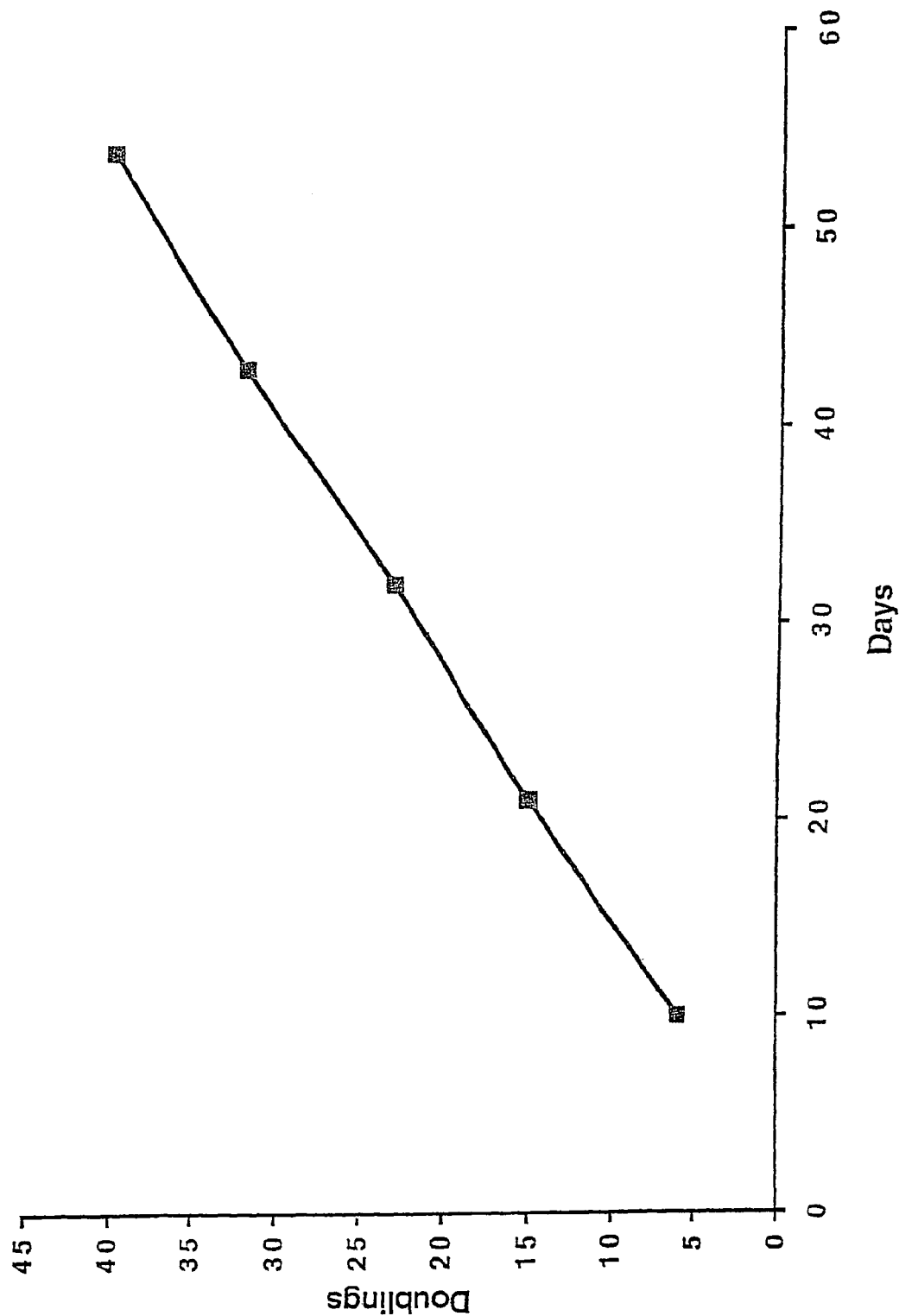
FIG. 4 illustrates the doubling rate of cell populations that co-express CD49c and CD90 cell population in culture.
Figure 5:
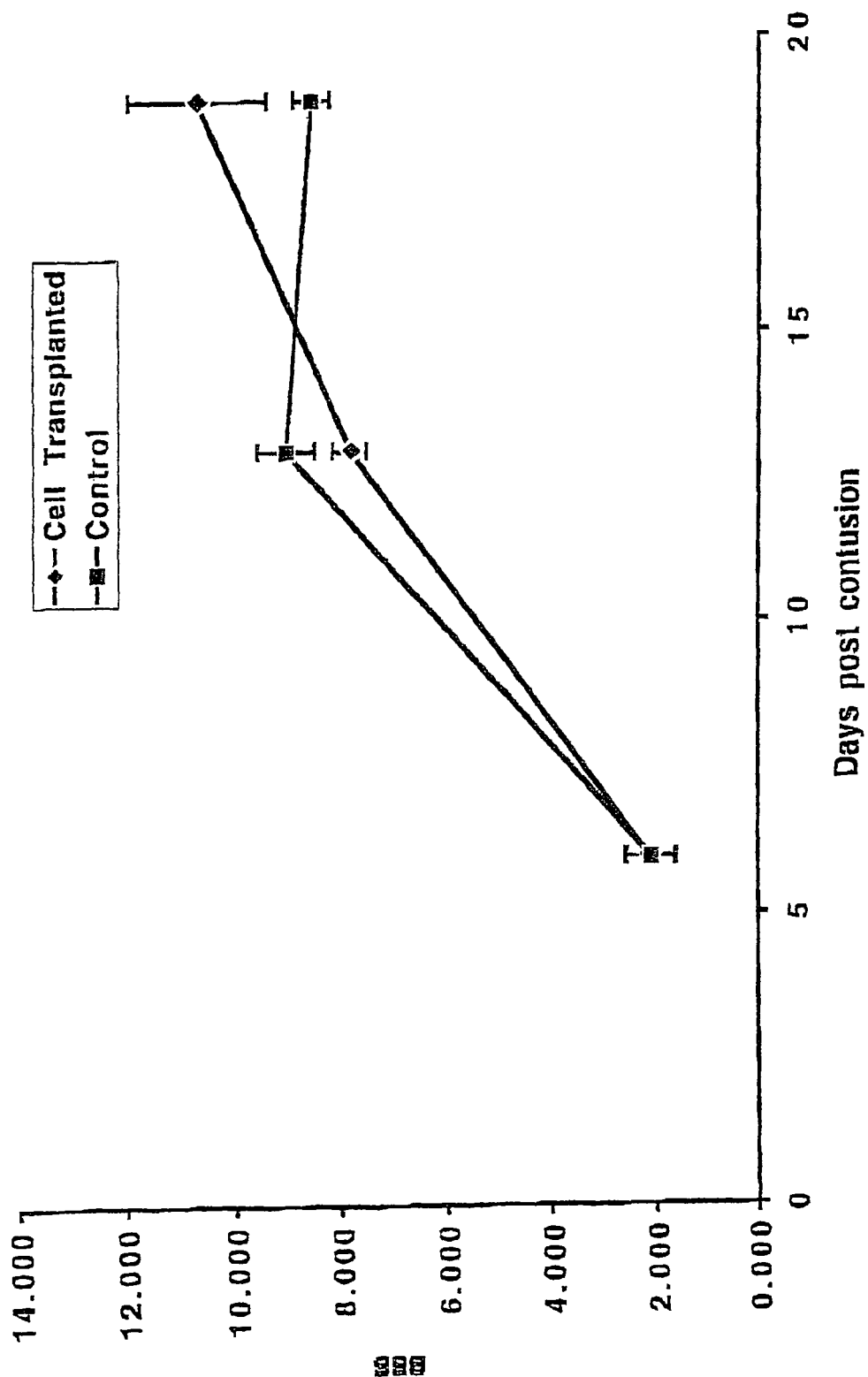
FIG. 5 illustrates the Basso-Beattie-Bresnahan (BBB) index for rats following spinal cord injury and after transplantation with a substantially homogenous cell population which co-express CD49c and CD90. At 19 days post contusion, rat received the cell transplantation showed greater improvement than rat received only PBS control.

The cell number generated from a single aliquot at the end of each successive expansion was determined by trypan exclusion and multiplied by the number of aliquots to calculate the yield (FIG. 3). Four successive expansions can potentially generate up to $1 \times 10^{17}$ cells from 25 mLs of bone marrow aspirate obtained from a single donor. The number of cell doublings was calculated from the cell yields using the following formula: (Log(end cell #)−Log(starting cell #)/Log(2) ("(2)" denotes doubling). The cell population underwent about 8 doublings during each expansion (FIG. 4). The doubling rate (# days in culture×24/doublings) was 30 hrs and remained constant for at least 50 doublings. Even after 30 doublings, the population uniformly retained the characteristic morphology of small, dividing cells without apparent evidence of the enlarged, flat morphology of aged or terminally-differentiated cells.

Example 5

Expression of Transcripts Encoding Regulators of Cell Growth and Osteoblast Differentiation by Cell Populations which Co-Express CD49c and CD90

The expression of transcripts for telomerase, p21, p53, CBFA1 and BSP were determined using quantitative polymerase chain reaction (qPCR). Briefly, Master Cell Bank of CFUs were derived from a bone marrow aspirate and stored as frozen aliquots using the method of Example 1. An aliquot was thawed, cultured at a density of 30 cells/cm$^2$ in tissue culture-treated T75 flasks in complete medium and incubated at 37° C. in an atmosphere consisting of 5% carbon dioxide, 5% oxygen, and 90% nitrogen/air.

After two weeks of culture, the cells were seeded in 96 well plates at 3000 cells/well. RNA was isolated using the QIAGEN RNeasy reagents and the Qiagen Biorobot 3000. An aliquot of the eluted RNA was used to synthesize cDNA. RNA was mixed with Promega MMLV, dNTPS, decamers and RNasin and incubated at 37° C. for 1 hour, followed by heat inactivation. For quantitative PCR, cDNA samples were combined with Applied Biosystems SYBR Green PCR Core reagents and amplicon specific primers, as described below, in a 384 well format. The 384 well plate was then transferred to the Applied Biosystems ABI Prism 7900 for qPCR analysis. The qPCR program entailed a 2 minute cycle at 50 degrees, followed by a 10 minute cycle at 95 degrees to activate the polymerase. This was than followed by 40 amplification cycles consisting of 15 seconds of melting at 95 degrees and one minute of extension/annealing at 60 degrees.

Cycle threshold values were converted into relative transcript number using a standard curve then normalized using the corresponding 18s. Data are expressed as a ratio of transcript per $10^6$ 18s transcripts. The name, Genebank ID, bp location and sequence of the qPCR primers are as follows:

```
18s-1F, K03432, 1742-1760 bp,
                                   (SEQ ID NO: 1)
5'-ATG GGG ATC GGG GAT TGC A-3';

18s-1R, K03432, 1871-1890 bp,
                                   (SEQ ID NO: 2)
5'-CCG ATC CGA GGG CCT CAC TA-3';

BSP-1F, NM000582, 483-508 bp,
                                   (SEQ ID NO: 3)
5'-CAC TCC AGT TGT CCC CAC AGT AGA CA3';
```

-continued

```
BSP-1R, 611-632 bp,
                                     (SEQ ID NO: 4)
5'-TCG CTT TCC ATG TGT GAG GTG A-3';

CBFA1-1F, L40992, 389-407 bp,
                                     (SEQ ID NO: 5)
5'-GGC CGG AGT GGA CGA GGC AA-3';

CBFA1-1R, L40992, 504-529 bp,
                                     (SEQ ID NO: 6)
5'-CAT CAA GCT TCT GTC TGT GCC TTC TG-3';

p21-1F, S67388, 52-72 bp,
                                     (SEQ ID NO: 7)
5'-ACC GAG GCA CTC AGA GGA GGC-3';

p21-1R, S67388, 171-191 bp,
                                     (SEQ ID NO: 8)
5'-GCC ATT AGC GCA TCA CAG TCG-3';

p53-qFP4, M14694, 521-545 bp,
                                     (SEQ ID NO: 9)
5'-GAT GTT TTG CCA ACT GGC CAA GAC C-3';

p53-qRP4, M14694, 674-698 bp,
                                     (SEQ ID NO: 10)
5'-AGG AGG GGC CAG ACC ATC GCT ATC T-3';

Telo-1F; AF015950, 1500-1525 bp,
                                     (SEQ ID NO: 11)
5'-ACA ACG AAC GCC GCT TCC TCA GGA AC-3';
and Telo-1R, AF015950, 1625-1650 bp,
                                     (SEQ ID NO: 12)
5'-GCC GGA ACA CAG CCA ACC CCT GG-3'.
```

Telomerase activity is necessary for maintaining telomeres, which are DNA sequences located at the ends of chromosomes. Since most human cells lack telomerase, the telomeres shorten with each division until the cells growth arrest (Harley, C. B., *Mutation Research* 256(2-6):271-282 (1991); Hara, E. et al., *Biochem Biophys Res Commun* 179 (1):528-534 (1991); Shay, J. W. et al., *Exp Cell Res* 196(1): 33-39 (1991)). Cell populations which co-express CD49c and CD90 express telomerase at the level of approximately 13 transcripts/$10^6$ transcripts of 18S rRNA, which is consistent with the finding that this cell population continued to proliferate at a constant rate.

The p53 tumor suppressor plays a key role in the cell's response to DNA damage and inactivation of this gene is an important step in carcinogenesis. p53 expression is upregulated in response to DNA damage. Its ability to prevent the proliferation of defective cells involves the activation of several growth arrest genes including p21 (Burns, T. F. et al., *Oncogene* 20(34):4601-4612 (2001)). The substantially homogenous cell population of the invention which co-express CD49c and CD90 expressed about 670 p53 transcripts/ $10^6$ transcripts of 18S rRNA. This level of p53 shows that the tumor suppressor p 53 was not induced.

p21 is a potent cell cycle inhibitor and its expression during the cell cycle is tightly regulated at the transcriptional level (Gartel, A. L. et al., *Exp Cell Res* 246(2):280-289 (1999)). p21 is induced in growth arrested cells in response to oxidative stress in addition to DNA damage (Yin, Y., et al., *Mol Carcinog* 24(1): 15-24 (1999)). The substantially homogenous cell population of the invention which co-express CD49c and CD90 expressed p21 about 1690 transcripts/$10^6$ transcripts of 18s rRNA. This level of p21 shows that p21 was not induced and is consistent with both a low level of p53 and the short doubling time measured in Example 4.

The transcription factor, CBFA1, is necessary for osteoblast differentiation and bone formation (Otto, F., *Cell* 89(5): 765-771 (1997)). Bone sialoprotein (BSP) is a prominent, mineral-associated protein in the extracellular matrix of bone and is expressed by fully differentiated osteoblasts (Benson, M. D., et al., *J Biol Chem* 275(18):13907-13917 (2000)). The substantially homogenous cell population of the invention which co-express CD49c and CD90 expressed about 130 CBFA1 transcripts/$10^6$ transcripts of 18S rRNA and BSP was absent, which show that the cell population of the invention represents a progenitor that has not significantly differentiated into osteoblasts. Osteoblast differentiation is described in Ducy, P., *Dev Dyn* 219(4):461-471 (2000)).

Example 6

Secretion of Neurotrophic Factors and Cytokines by a Substantially Homogenous Cell Population which Co-Express CD49c and CD90

An aliquot of the Master Cell Bank generated in Example 1 was thawed and plated onto T75 flasks at 2500 cells/cm² with complete medium and incubated at 5% $O_2$. The following day the medium was removed and replaced with fresh complete medium. The supernatant was collected 8 hours later from T75 and the cells were counted (Cell count=280, 000 cells). The supernatant was aliquoted to 1 ml tubes and stored at −20° C. Another T75 was processed the same way 3 days later (Cell count=2.43 million). Supernatants were later thawed at room temperature and assayed by ELISA for secretion of the following neurotrophicfactors/cytokines using commercially available kits: BDNF (Chemicon), NGF (Chemicon), MCP-1 (R and D Systems), and IL-6 (R and D Systems). Multiple dilutions were performed on supernatant to ensure that measured values fell within standard ranges of the assay. In addition, media obtained from control cells secreting previously determined amounts of cytokine were run in parallel to assure assay validity. Values were obtained by normalizing raw data derived from ELISA to standard time (24 hours) and cell number (1 million) and are thus expressed as "picograms of cytokine secreted per 1 million cells per 24 hour period as follows:

| Cytokine | Amount Secreted (pg/$10^6$ cells/day |
|---|---|
| MCP-1 | 1009.15 |
| IL-6 | 18567.60 |
| BDNF | 8.88 |
| NGF | 80.12 |

Example 7

Transplantation of a Substantially Homogenous Cell Population of the Invention which Co-Express CD49c and CD90 into an Acute Rat Spinal Cord Injury Model Following traumatic injury to the spinal cord neuronal death, inflammation and progressive loss of damaged neurons ensue overtime. A substantially homogenous cell population of the invention which co-express CD49c and CD90 improved outcome during acute neurologic injury. A cell population prepared as described in Example 1 was transplanted into contused spinal cord of adult female Sprague-Dawley rats.

The thoracic spinal cord of Sprague-Dawley rats was exposed by laminectomy at the level of T10 under general anesthesia. After the laminectomy is completed, a 10 gm rod was dropped from a height of 25 mm to produce a spinal cord injury of moderate severity onto the exposed spinal cord using the NYU spinal cord impactor (Constantini, S. et al., *J Neurosurg* 80(1):97-111 (1994)). During surgery, the body temperature of the rats was kept at 37° C. During recovery, rats were placed overnight in a temperature and humidity controlled chamber. Seven days after impact injury, the spinal cords were re-exposed. Using a 50 mL gas tight Hamilton syringe (VWR Scientific Products, Bridgeport, N.J.) with a 30 gauge needle, 250,000 cells of the invention at a concentration of 25,000/µl were transplanted into the spinal cord. The cells were injected into the epicenter of the syrinx at the T10 level at a rate of 2 mL/minute. The needle was left in place for additional 5 minutes before it was removed from the spinal cord. Following surgery, all animals received methylprednisolone (30 mg/kg, i.v.) immediately following surgery. To prevent immun-rejection, Cyclosporin A (CsA) was given subcutaneously at 10 mg/kg 3 days prior to the day of transplantation and maintained thereafter.

The Basso-Beattie-Bresnahan openfield locomotor test (BBB Test) (Basso, D. B. et al., *J Neurotrauma* 12(1):1-21 (1995)) were performed the day before transplantation (day 6 after injury). Behavioral testing was performed for each hindlimb weekly using the BBB scores. Scoring was performed blinded to the treatment status. At 19 days after contusion, animals that had received a substantially homogenous population of cells which co-express CD49c and CD90, showed greater improvement on the BBB score than animals received only PBS (10.6±1.2 vs 8.5±0.3).

At 2 weeks after transplantation, contused spinal cords from some animals were removed and examined for evidence on nerve fiber regeneration. SMI 32 (Sternberger Monoclonals, Inc, Lutherville, Md.) antibody was used to immunostain for regenerating fibers in the syrinx at a dilution of 1:4000. Numerous fibers were observed growing into the contused syrinx.

Example 8

Expression of Transcripts Encoding Regulators of Neuronal Differentiation by a Substantially Homogenous Population of Cells which Co-Express CD49c and CD90

The expression of transcripts for Sox-2 and Musashi were determined using quantitative polymerase chain reaction (qPCR). Briefly, Master Cell Bank of CFUs were derived from a bone marrow aspirate and stored as frozen aliquots using the method of Example 1. An aliquot was thawed and the cells were seeded in 96 well plates at 2000 cells/well in complete media and incubated at 37° C. in an atmosphere consisting of 5% carbon dioxide, 5% oxygen and 90% nitrogen/air for 3 days. On the third day of culture, cells were treated with 5 µM nifedipine (an L-type calcium channel blocker). After 24 hours of treatment, RNA was isolated using the QIAGEN®RNeasy reagents and the Qiagen Biorobot 3000. An aliquot of the eluted RNA was used to synthesize cDNA. Specifically, RNA was mixed with Promega MMLV, dNTPS, decamers and RNasin and incubated at 37° C. for 1 hour, followed by heat inactivation.

For quantitative PCR, cDNA samples were combined with Applied Biosystems SYBR Green PCR Core reagents and amplicon specific primers, as described below, in a 384 well format. The 384 well plate was then transferred to the Applied Biosystems ABI Prism 7900 for qPCR analysis. The qCPR program entailed a 2 minute cycle at 50 degrees, followed by a 10 minute cycle at 95 degrees to activate the polymerase. This was then followed by 40 amplification cycles consisting of 15 seconds of melting at 95 degrees and one minute of extension/annealing at 60 degrees. Cycle threshold values were converted into relative transcript number using a standard curve then normalized using the corresponding 18s. Data are expressed as a ratio of transcript per $10^6$ 18s transcripts.

The name, Genebank ID, bp location and sequence of the qPCR primers are as follows:

```
18s-1F, K03432, 1742-1760 bp,
                                    (SEQ ID NO: 1)
5'-ATG GGG ATC GGG GAT TGC A-3';

18s-1R, K03432, 1871-1890 bp,
                                    (SEQ ID NO: 2)
5'-CCG ATC CGA GGG CCT CAC TA-3';

Sox-2F, Z31560, 517-541 bp,
                                   (SEQ ID NO: 13)
5'-GGC AGC TAC AGC ATG ATG CAG GAC C-3';

Sox-2R, 624-647 bp,
                                   (SEQ ID NO: 14)
5'-CTG GTC ATG GAG TTG TAC TGC AGG-3';

Musashi-1F, AB012851, 370-389 bp,
                                   (SEQ ID NO: 15)
5'-CAA GAT GGT GAC TCG AAC GA-3';

Musashi-1R, 480-499 bp,
                                   (SEQ ID NO: 16)
5'-GGT TTT GTC AAA CAT CAG CA-3'.
```

The gene Sox-2 encodes a conserved nuclear transcription factor related to the Mammalian Testis Determining Gene that is expressed throughout the neural tube during brain development and is essential for the survival of primitive neural ectoderm (Uwanogho, *Mech. Dev.* 49:23-36 (1995)). In addition, expression of Sox-2 persists beyond development in restricted populations of adult neural stem cells, suggesting a further role for this factor in regulating neural fate (Zappone, *Development* 127:2367-2382 (2000)). Under unstimulated conditions in complete media, the cells which co-express CD49c and CD90 expressed approximately 4 Sox-2 transcripts/$10^6$ transcripts of 18S RNA. However, in response to nifedipine, the cells which co-express CD49c and CD90 expressed 28 Sox-2 transcripts/$10^6$ transcripts of 18S RNA, an approximate 7-fold increase. This increase in Sox-2 expression suggests that, in response to certain epigenetic treatments, the cells which co-express CD49c and CD90 may display traits associated with early neural populations.

The gene Musashi encodes an RNA-binding protein that is highly expressed within the developing nervous system and, like Sox-2, is also expressed in mammalian neural stem cells (Sakakibara, *Dev Biol* 176:230-242 (1996)). Furthermore, expression of Musashi is required for normal development of multiple neuronal population (Nakamura, *Neuron* 13:67-81 (1994)). Under unstimulated conditions in complete media, the cells which co-express CD49c and CD90 expressed approximately 0.005 Musashi transcripts/$10^6$ transcripts of 18S RNA. However, in response to 24 hours of stimulation with nifedipine, the cells which co-express CD49c and CD90 expressed 0.093 transcripts/$10^6$ transcripts of 18S RNA, an approximate 17-fold increase. This increase in Sox-2 expression suggests that, in response to certain epigenetic treatments, the cells which co-express CD49c and CD90 may display traits associated with early neural populations.

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. A method of producing an isolated cell population wherein greater than about 91% of the cells in said cell population co-express CD49c and CD90, comprising the steps of:
   a) providing a source population of cells; and,
   b) culturing said source cell population at a seeding density of less than about 100 cells/cm² under a low oxygen condition.

2. The method of claim 1, wherein the source of the cell population is bone marrow.

3. The method of claim 2, wherein the bone marrow is human bone marrow.

4. The method of claim 1, wherein the low oxygen condition is less than about 15% oxygen.

5. The method of claim 4, wherein the low oxygen condition is less than about 10% oxygen.

6. The method of claim 1, wherein the low oxygen condition is about 5% oxygen.

7. The method of claim 2, further including lysing the red blood cells in the bone marrow prior to culturing the cells of the bone marrow.

8. The method of claim 2, further including fractionating the bone marrow prior to culturing the bone marrow.

9. The method of claim 8, wherein in the bone marrow is fractionated by passage through a density gradient.

10. The method of claim 8, wherein the bone marrow is fractionated by NH₂Cl lysis.

11. The method of claim 8, wherein the bone marrow is fractionated by fluorescent activated sorting.

12. The method of claim 8, wherein the bone marrow is fractionated by magnetic sorting.

13. The method of claim 1, wherein the cells which co-express CD49c and CD90 do not express CD34 and/or CD45.

14. The method of claim 1, wherein the cells isolated from the cultured source express at least one trophic factor selected from the group consisting of:
   a) brain-derived neurotrophic factor (BDNF);
   b) interleukin-6 (IL-6);
   c) nerve growth factor (NGF);
   d) macrophage chemoattractant protein-1 (MCP-1);
   e) neurotrophin-3 (NT-3);
   f) interleukin-7 (IL-7);
   g) interleukin-11 (IL-11);
   h) stem cell factor (SCF);
   i) matrix metalloproteinase-9 (MMP-9); and,
   j) Cystatin-C.

15. A method of producing an isolated cell population wherein greater than about 91% of the cells in said cell population co-express CD49c and CD90, comprising the steps of:
   a) providing a source population of cells; and,
   b) culturing said source cell population at a seeding density of less than about 100 cells/cm² under a low oxidative stress condition.

16. The method of claim 15, wherein the source of the cell population is bone marrow.

17. The method of claim 15, wherein the bone marrow is human bone marrow.

18. A method of producing an isolated cell population wherein greater than about 91% of the cells in said cell population co-express CD49c and CD90, comprising the steps of:

a) providing a source population of cells; and,
b) culturing said source cell population at a seeding density of less than about 50 cells/cm² under a low oxidative stress condition.

19. A method of producing an isolated cell population wherein greater than about 91% of the cells in said cell population co-express CD49c and CD90, comprising the steps of:
a) providing a source population of cells; and,
b) culturing said source cell population at a seeding density of less than about 30 cells/cm² under a low oxidative stress condition.

20. A method of producing an isolated cell population wherein greater than about 91% of the cells in said cell population co-express CD49c and CD90, comprising the steps of:
a) providing a source population of cells; and,
b) culturing said source cell population at a seeding density of less than about 50 cells/cm² under a low oxygen condition.

21. A method of producing an isolated cell population wherein greater than about 91% of the cells in said cell population co-express CD49c and CD90, comprising the steps of:
a) providing a source population of cells; and,
b) culturing said source cell population at a seeding density of less than about 30 cells/cm² under a low oxygen condition.

22. The method of claim 1, wherein the low oxygen condition is between about 1% to about 10% oxygen.

23. The method of claim 1, wherein the low oxygen condition is between about 2% to about 7% oxygen.

24. The method of claim 20, wherein the source of the cell population is bone marrow.

25. The method of claim 24, wherein the bone marrow is human bone marrow.

26. The method of claim 20, wherein the low oxygen condition is less than about 15% oxygen.

27. The method of claim 26, wherein the low oxygen condition is less than about 10% oxygen.

28. The method of claim 20, wherein the low oxygen condition is about 5% oxygen.

29. The method of claim 20, wherein the low oxygen condition is between about 1% to about 10% oxygen.

30. The method of claim 20, wherein the low oxygen condition is between about 2% to about 7% oxygen.

31. The method of claim 24, further including lysing the red blood cells in the bone marrow prior to culturing the cells of the bone marrow.

32. The method of claim 24, further including fractionating the bone marrow prior to culturing the bone marrow.

33. The method of claim 32, wherein in the bone marrow is fractionated by passage through a density gradient.

34. The method of claim 32, wherein the bone marrow is fractionated by NH₂Cl lysis.

35. The method of claim 32, wherein the bone marrow is fractionated by fluorescent activated sorting.

36. The method of claim 32, wherein the bone marrow is fractionated by magnetic sorting.

37. The method of claim 20, wherein the cells which co-express CD49c and CD90 do not express CD34 and/or CD45.

38. The method of claim 20, wherein the cells isolated from the cultured source express at least one trophic factor selected from the group consisting of:
a) brain-derived neurotrophic factor (BDNF);
b) interleukin-6 (IL-6);
c) nerve growth factor (NGF);
d) macrophage chemoattractant protein-1 (MCP-1);
e) neurotrophin-3 (NT-3);
f) interleukin-7 (IL-7);
g) interleukin-11 (IL-11);
h) stem cell factor (SCF);
i) matrix metalloproteinase-9 (MMP-9); and,
j) Cystatin-C.

39. The method of claim 21, wherein the source of the cell population is bone marrow.

40. The method of claim 39, wherein the bone marrow is human bone marrow.

41. The method of claim 21, wherein the low oxygen condition is less than about 15% oxygen.

42. The method of claim 41, wherein the low oxygen condition is less than about 10% oxygen.

43. The method of claim 21, wherein the low oxygen condition is about 5% oxygen.

44. The method of claim 21, wherein the low oxygen condition is between about 1% to about 10% oxygen.

45. The method of claim 21, wherein the low oxygen condition is between about 2% to about 7% oxygen.

46. The method of claim 40, further including lysing the red blood cells in the bone marrow prior to culturing the cells of the bone marrow.

47. The method of claim 40, further including fractionating the bone marrow prior to culturing the bone marrow.

48. The method of claim 47, wherein the bone marrow is fractionated by passage through a density gradient.

49. The method of claim 47, wherein the bone marrow is fractionated by NH₂Cl lysis.

50. The method of claim 47, wherein the bone marrow is fractionated by fluorescent activated sorting.

51. The method of claim 47, wherein the bone marrow is fractionated by magnetic sorting.

52. The method of claim 21, wherein the cells which co-express CD49c and CD90 do not express CD34 and/or CD45.

53. The method of claim 21, wherein the cells isolated from the cultured source express at least one trophic factor selected from the group consisting of:
a) brain-derived neurotrophic factor (BDNF);
b) interleukin-6 (IL-6);
c) nerve growth factor (NGF);
d) macrophage chemoattractant protein-1 (MCP-1);
e) neurotrophin-3 (NT-3);
f) interleukin-7 (IL-7);
g) interleukin-11 (IL-11);
h) stem cell factor (SCF);
i) matrix metalloproteinase-9 (MMP-9); and,
j) Cystatin-C.

54. A method of producing an isolated cell population wherein greater than about 91% of the cells in said cell population co-express CD49c and CD90 and maintain a constant population doubling rate for at least 8 population doublings, comprising the steps of:
a) providing a source population of cells; and,
b) culturing said source cell population at a seeding density of less than about 100 cells/cm² under a low oxygen condition.

55. The method of claim 54, wherein the self-renewing colony forming units of cells maintain a constant population doubling rate for at least 16 population doublings.

56. The method of claim 55, wherein the self-renewing colony forming units of cells maintain a constant population doubling rate for at least 24 population doublings.

57. The method of claim 56, wherein the self-renewing colony forming units of cells maintain a constant population doubling rate for at least 32 population doublings.

58. The method of claim 57, wherein the self-renewing colony forming units of cells maintain a constant population doubling rate for at least 40 population doublings.

59. The method of claim 54, wherein the seeding density is less than about 50 cells/cm$^2$.

60. The method of claim 59, wherein the seeding density is less than about 30 cells/cm$^2$.

61. The method of claim 54, wherein the low oxygen condition is less than about 15% oxygen.

62. The method of claim 61, wherein the low oxygen condition is less than about 10% oxygen.

63. The method of claim 54, wherein the low oxygen condition is about 5% oxygen.

64. The method of claim 54, wherein the low oxygen condition is between about 1% to about 10% oxygen.

65. The method of claim 54, wherein the low oxygen condition is between about 2% to about 7% oxygen.

66. The method of claim 54, wherein the source of the cell population is bone marrow.

67. The method of claim 66, wherein the bone marrow is human bone marrow.

68. The method of claim 67, wherein the population doubling rate less than about 30 hours.

\* \* \* \* \*

```
                        SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide primers

<400> SEQUENCE: 1
atggggatcg gggattgca                                                    19

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 2
ccgatccgag ggcctcacta                                                   20

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide primers

<400> SEQUENCE: 3
cactccagtt gtccccacag tagaca                                            26

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide primers

<400> SEQUENCE: 4
tcgctttcca tgtgtgaggt ga                                                22

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 5
ggccggagtg gacgaggcaa                                                   20

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide primers

<400> SEQUENCE: 6
```

```
catcaagctt ctgtctgtgc cttctg                                          26

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primers

<400> SEQUENCE: 7
accgaggcac tcagaggagg c                                               21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primers

<400> SEQUENCE: 8
gccattagcg catcacagtc g                                               21

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primers

<400> SEQUENCE: 9
gatgttttgc caactggcca agacc                                           25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide primers

<400> SEQUENCE: 10
aggaggggcc agaccatcgc tatct                                           25

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide primers

<400> SEQUENCE: 11
acaacgaacg ccgcttcctc aggaac                                          26

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primers

<400> SEQUENCE: 12
gccggaacac agccaacccc tgg                                             23

<210> SEQ ID NO 13
<211> LENGTH: 25
<212> TYPE: DNA
<213> ORGANISM: Artificial Sequence
<220> FEATURE:
```

```
<223> OTHER INFORMATION: Oligonucleotide primers

<400> SEQUENCE: 13
ggcagctaca gcatgatgca ggacc                                            25

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide primers

<400> SEQUENCE: 14
ctggtcatgg agttgtactg cagg                                             24

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 15
caagatggtg actcgaacga                                                  20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 16
ggttttgtca aacatcagca                                                  20
```